United States Patent
Ziaie et al.

(10) Patent No.: US 7,988,685 B2
(45) Date of Patent: Aug. 2, 2011

(54) HYDROGEL COMPOSITIONS, DEVICES, AND MICROSCALE COMPONENTS

(75) Inventors: Babak Ziaie, St. Paul, MN (US); Ronald A. Siegel, Minneapolis, MN (US); Yuandong Gu, Plymouth, MN (US); Antonio Baldi, Sant Cugat del Valles (ES); Gauri P. Misra, New Delhi (IN); Paul E. Loftness, Gibbon, MN (US); Ming Lei, St. Paul, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 1934 days.

(21) Appl. No.: 10/494,119

(22) PCT Filed: Nov. 1, 2002

(86) PCT No.: PCT/US02/35159
§ 371 (c)(1),
(2), (4) Date: Jul. 29, 2004

(87) PCT Pub. No.: WO03/051286
PCT Pub. Date: Jun. 26, 2003

(65) Prior Publication Data
US 2004/0248326 A1 Dec. 9, 2004

Related U.S. Application Data

(60) Provisional application No. 60/335,164, filed on Nov. 1, 2001.

(51) Int. Cl.
*A61M 5/00* (2006.01)
*H01L 21/00* (2006.01)
*H01L 21/76* (2006.01)

(52) U.S. Cl. .......... 604/890.1; 438/1; 427/2.11
(58) Field of Classification Search .......... 604/21, 604/131, 890.1–892.1; 600/309, 345
See application file for complete search history.

(56) References Cited

U.S. PATENT DOCUMENTS

| | | | |
|---|---|---|---|
| RE33,899 E * | 4/1992 | Tyer | 210/220 |
| 5,869,077 A | 2/1999 | Dionne et al. | |
| 6,167,910 B1 * | 1/2001 | Chow | 137/827 |
| 6,200,643 B1 * | 3/2001 | Sugai et al. | 427/475 |
| 6,488,872 B1 * | 12/2002 | Beebe et al. | 264/31 |
| 6,751,491 B2 * | 6/2004 | Lew et al. | 600/345 |
| 7,244,232 B2 * | 7/2007 | Connelly et al. | 600/309 |
| 2001/0031740 A1 | 10/2001 | Unger et al. | |
| 2002/0082543 A1 * | 6/2002 | Park et al. | 604/21 |
| 2004/0238052 A1 * | 12/2004 | Karp et al. | 137/822 |
| 2009/0018413 A1 * | 1/2009 | Santini et al. | 600/309 |

OTHER PUBLICATIONS

Connelly et al., Process for Identifying Cancerous and/or Metastatic Cells of a Living Organism, Jul. 30, 2001, U.S. Appl. No. 60/308,628 Drawings and Specification.*

(Continued)

*Primary Examiner* — Theodore J Stigell
*Assistant Examiner* — Imani Hayman
(74) *Attorney, Agent, or Firm* — Fish & Richardson P.C.

(57) ABSTRACT

The invention provides hydrogel compositions, components, and hydrogel-actuated or mediated devices, and methods for the incorporation of hydrogel microscale components in microscale devices and systems. The methods and devices result in active microvalves that are useful in microfluidic applications, including analyte sensing, in process chemical and fermentation stream monitoring, and drug delivery. In particular, the devices are useful for controlled drug delivery either in response to a pre-determined stimulus or for pulsatile delivery.

13 Claims, 25 Drawing Sheets

OTHER PUBLICATIONS

Lew et al., Substance Sensing System Using a Hydrogel Chip and Displacement Measuring System, Sep. 1, 2001, U.S. Appl. No. 60/316,731 Specification.*

Park et al., Microneedle Devices and Production Thereof, Dec. 14, 2000, U.S. Appl. No. 60/255,603 Specification.*

* cited by examiner

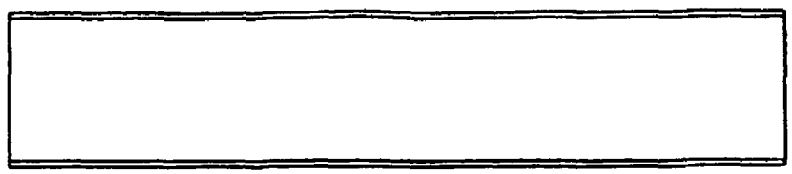
FIG. 4a
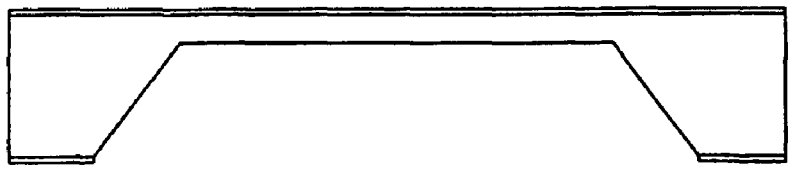
FIG. 4b
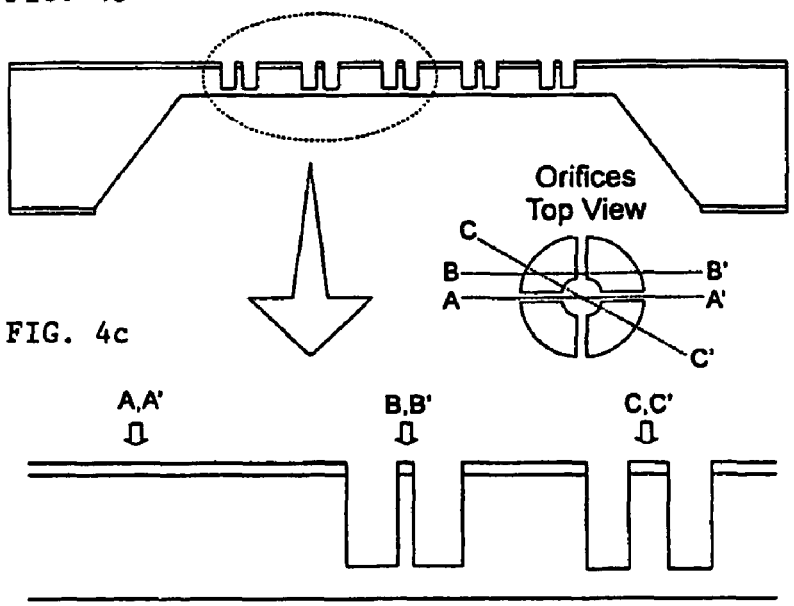
FIG. 4c
FIG. 4d
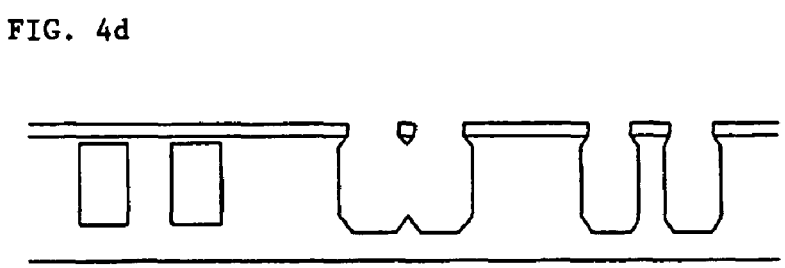
FIG. 4e
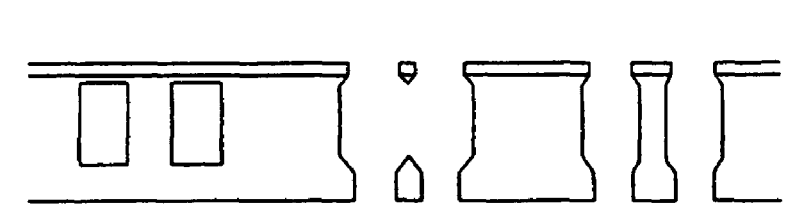
FIG. 4f

HYDROGEL COMPOSITIONS, DEVICES, AND MICROSCALE COMPONENTS

CROSS-REFERENCE TO RELATED APPLICATIONS

This application is a National Stage application under 35 U.S.C. §371 and claims the benefit under 35 U.S.C. §119(a) of International Application No. PCT/US02/35169 having an International Filing Date of Nov. 1, 2002, which claims the benefit of priority of U.S. Provisional Application Ser. No. 60/335,164 having a filing date of Nov. 1, 2001, both of which are incorporated herein in their entirety.

TECHNICAL FIELD

This invention relates to hydrogel compositions, components, and hydrogel-actuated or mediated devices, and methods for the incorporation of hydrogel microscale components in microscale devices and systems.

BACKGROUND

Microscale systems that contain integrated structural and functional microscale components such as pumps, valves, channels, and sensors are highly desirable in microfluidics applications, including chemical and fermentation stream monitoring, physiologic analyte monitoring, drug delivery, and lab-on-a-chip applications. Microscale components result in reduced sample and waste volumes, features that are particularly useful when sample availability, sample expense, waste disposal costs, or safety are a concern. Incorporation of microscale components into analyte-sensing devices can facilitate the detection of multiple analytes from a single small sample. Highly integrated systems can allow a controlled response to a particular analyte, for example, by coupling the delivery of a particular compound with the detection of the analyte. Such systems have wide applicability across the environmental, chemical, medical, and biotechnological fields.

Current manufacturing and assembly methods for microscale systems rely on scaled-down versions of macroscale processes, resulting in limited flexibility of design, high cost, and long development times. For example, the micron-range size of the components makes handling difficult; electrostatic, surface, and other physical forces can become dominant, thereby impeding effective manipulation of the components. Integration of multiple microscale components into a single device can represent a further challenge.

Active microscale valves are desirable components in microscale devices and systems. Conventional active microvalves couple a flexible diaphragm or membrane to an actuator that deflects the diaphragm or membrane in response to temperature or electromagnetic fields. Unfortunately, at the small sizes used in microscale devices, these valves may require undesirably high power consumption. It would be useful to reduce the power consumption required in microscale devices yet retain the active microvalve functionality. It would also be useful to have methods and devices that incorporate active microvalves in controlled drug delivery applications.

SUMMARY

The present invention relates to hydrogel compositions, components, and hydrogel-actuated or mediated devices, and methods for the incorporation of hydrogel microscale components in microscale devices and systems. The methods and devices of the present invention are useful in the chemical, environmental, medical, and biotechnological fields for a variety of analyte testing or drug delivery applications.

Accordingly, it is one object of the invention to provide microscale components. The microscale components generally include substrates having orifices, openings, or channels to allow fluid to flow through the substrate. The substrate can be, without limitation, glass, plastic, silicon, or a transparent mineral. In one embodiment, the substrate is glass. The substrate can have a cross-section depth of about 100-1000 µm.

Fluid flow through the orifices, openings, or channels in the substrates may be regulated (e.g., flow controlled) by hydrogels. The hydrogel is capable of undergoing a reversible volume change in response to a predetermined stimulus in a medium contacting the hydrogel. The reversible volume change can lead to a reversible gating of a channel or orifice (e.g., blocking access to a channel, allowing access to a channel), allowing the microscale components to act as active microvalves. The volume change can be an increase or a decrease in volume. For example, a 3-methacrylamidophenylboronic acid hydrogel will undergo a volume increase in response to glucose, while a 3-acrylamido-4-nitrobenzeneboronic acid hydrogel will undergo a volume decrease. Generally, the volume responsive hydrogel will have a thickness of from about 20 µm to about 1 mm.

The hydrogels of the present invention are generally formed by the polymerization of a liquid polymerizable mixture. The liquid polymerizable mixture can include a comonomer, a cross-linker, and optionally a buffer and/or a solvent. The liquid polymerizable mixture may optionally include a responsive composition. The responsive composition can be 3-methylacrylamidophenylboronic acid. Alternatively, the responsive composition can be 3-acrylamido-4-nitrobenzeneboronic acid. The liquid polymerizable mixture can include, for example, 3-methylacrylamidophenylboronic acid, a comonomer, and a crosslinker. In one embodiment, the liquid polymerizable mixture can include about 5 to about 25 mol % 3-methylacrylamidophenylboronic acid, about 75 to about 95 mol % acrylamide, and about 0.1 to about 1 mol % N,N'-methylenebisacrylamide. In another embodiment, the liquid polymerizable mixture can include about 5 to about 25 mol % 3-acrylamido-4-nitrobenzeneboronic acid, about 75 to about 95 mol % acrylamide, and about 0.1 to about 1 mol % N,N'-methylenebisacrylamide.

The predetermined stimulus to which the hydrogel is responsive can be a physical change, a chemical change, a chemical compound, or a biological agent. The physical change can be a temperature change, an electric field change, a change in light absorption, a change in light emission, a magnetic field change, and a pressure change. The chemical change can be, for example, a pH change or an ionic strength change. The predetermined stimulus alternatively can be a chemical compound in the medium contacting the hydrogel. The chemical compound can be, for example, glucose, lactate, lactic acid, ethanol, glycerol, or ammonia. The predetermined stimulus can also be a biological agent in the medium contacting the polymer gel. The biological agent can be, for example, a toxin, a pathogen, a protein, an antibody, an antigen, a virus, a peptide, a carbohydrate, a lipid, or a nucleic acid.

In one embodiment of microscale component according to the present invention, a microscale component includes a substrate having a first set of one or more microscale channels on a first surface of the substrate, with the channels of the first set having a depth of more than half of the cross-section depth of the substrate. The microscale component includes a second set of one or more microscale channels on a second surface of the substrate, with the channels of the second set having a depth of more than half of the cross-section depth of the substrate, and the second set in an orientation to the first set to allow the first and second sets to intersect. The microscale component can further include a hydrogel at the intersection of the first and second sets of microscale channels.

In another embodiment, a microscale component includes a substrate having a substrate member that substantially spans the cross-sectional depth of the substrate. The substrate member has an axis substantially perpendicular to a surface of the substrate, and has a plurality of radial projections that span a portion of the cross-sectional depth of the substrate. A hydrogel may be positioned adjacent to the substrate member and radial projections in the microscale component, allowing the hydrogel to be tethered to one or more of the substrate member and radial projections.

It is a further object of the present invention to provide an implantable medical device that contains a microscale component as an active microvalve. The implantable medical device can include a drug reservoir that is in communication with or is capable of delivering a drug, e.g., insulin, to the microscale component. For example, the drug reservoir can communicate with the microscale component through a catheter, e.g, a catheter implanted subcutaneously, intraperitoneally, or intravascularly.

The implantable device can further include a pump to deliver the drug from the drug reservoir to the microscale component. In one embodiment, useful for the treatment of diabetes, a pump capable of delivering insulin is in communication with the hydrogel microscale component.

It is another object of the invention to provide an implantable microscale system for drug delivery to a patient. The system includes a microscale component according to the present invention; a catheter, with one end of the catheter, in communication with the microscale component; a drug reservoir in communication with the second end of the catheter; and a pump capable of delivering the drug (e.g., insulin) from the reservoir through the catheter to the microscale device. The end of the catheter in communication with the microscale component may be positioned intraperitoneally, subcutaneously, or intravascularly in the patient. The pump may be a volatile liquid/bellows pump, an electromechanical pump, or an osmotic pump.

In another aspect of the invention, a glucose-sensitive hydrogel microscale component is used to monitor a fermentation stream to control the delivery of glucose to the fermentation system. In one embodiment, a glucose-sensitive hydrogel microscale component acts as an active microvalve to regulate the delivery of a glucose solution to a fermentation stream depending on the level of glucose in the stream.

Another object of the present invention is to provide an implantable, hydrogel-actuated microvalve. The hydrogel-actuated microvalve mechanically couples the volume-change of a hydrogel in response to a predetermined chemical compound to the opening and closing of an orifice or a channel by a membrane, member, or body. In one embodiment, an implantable, hydrogel-actuated microvalve can include a first substrate permeable to a predetermined chemical compound; a volume-responsive hydrogel is adjacent to the permeable first substrate and can undergo a volume change in response to the predetermined chemical compound. The term "adjacent" as used herein means proximal positioning over at least a portion of the respective surfaces. A second substrate is adjacent to the volume-responsive hydrogel and is deformable (e.g., can deflect) in response to the volume-responsive hydrogel; a third substrate is adjacent to the second substrate and includes an orifice capable of being sealed by the second substrate upon the deformation of the second substrate.

In another embodiment, an implantable, hydrogel-actuated microvalve includes a first substrate permeable to a predetermined chemical compound; a volume-responsive hydrogel is adjacent to the permeable first substrate and can undergo a volume change in response to the predetermined chemical compound. A second substrate is adjacent to the volume-responsive hydrogel and is deformable (e.g., can deflect) in response to the hydrogel. A third substrate is adjacent to the second substrate and includes a member. The member is moveable in response to deformation of the second substrate. A fourth substrate is adjacent to the third substrate and includes an orifice capable of being sealed by the member of the third substrate upon movement of the member.

In yet another embodiment, an implantable hydrogel-actuated microvalve includes a first substrate permeable to a predetermined chemical compound; a volume-responsive hydrogel is adjacent to the permeable first substrate and can undergo a volume change in response to the predetermined chemical compound. A second substrate is adjacent to the volume-responsive hydrogel and is deformable (e.g., can deflect) in response to the volume-responsive hydrogel. A third substrate is adjacent to the second substrate and includes a member; the member is moveable in response to deformation of the second substrate. A fourth substrate is adjacent to the third substrate and includes a flexible body to control access, upon movement of the member, to a channel disposed between the third substrate and the fourth substrate.

In the implantable, hydrogel-actuated microvalves of the present invention, the first substrate should be resistant to deformation. The first substrate can be a porous plate. The porous plate can include homogenous pores. The pores can be in the range of about 10 nm to about 50 µm. The porous plate can have a thickness of about 50-1000 µm. In one embodiment, a porous glass plate (Vycore® 7930) is used. In another embodiment, a porous aluminum oxide plate (Anapore®) is used.

The second substrate can deform by deflection towards or away from the third substrate. The deflection can range from about 10 to about 500 µm. The second substrate should be biocompatible and/or pharmaceutically acceptable. The second substrate can be any reversibly deformable elastomer. For example, the second substrate can be a low modulus silicone, neoprene, or isoprene rubber. If a low modulus silicone rubber membrane is used, it may be produced by spin-coating silicone rubber on a silicon wafer. The silicon wafer may be removed entirely or in selective regions by deep etching or base (KOH) etching.

In some embodiments, the third substrate may include a member. The third substrate may move in response to the deformation of the second substrate. The member may be silicon or glass.

The fourth substrate may include a flexible body to control access to a channel disposed between the third and fourth substrates. The flexible body may flex in response to the movement of the member of the third substrate. Upon movement of the flexible body, access to the channel may be available.

It is another object of the invention to provide implantable medical devices that contain hydrogel-actuated microvalves. In one embodiment, a catheter may include an embodiment of the hydrogel-actuated microvalves of the present invention.

Another aspect of the present invention is to provide methods for manufacturing a microscale component of a microscale device. In one embodiment, the method involves providing a substrate and forming a first set of microscale channels on a first surface of the substrate so that the channels have a depth of more than half of the cross-section depth of the substrate. A second set of microscale channels on a second surface of the substrate is also formed with a depth of more than half of the cross-section depth of the substrate; the second set is in an orientation to the first set to allow the first and second sets to intersect. A liquid polymerizable mixture may be introduced into the first and second sets of microscale channels and polymerized; and residual unreacted liquid polymerizable mixture removed to provide a hydrogel at the intersection of the first and second sets. By this means, a hydrogel that both spans the substrate and is also physically entrapped (e.g., strapped) in the substrate is provided.

The first and second set of channels can be formed by processes such as lithography or deep trench etching. The second set of one or more microscale channels can be in a orientation perpendicular to the first set. The microscale channels of the first and second sets can have an aspect ratio (width to height ratio) of from about 10:1 to about 1:10. Alternatively, the aspect ratio can range from about 5:1 to about 1:5. In one embodiment, the aspect ratio is about 1:3.

In another embodiment of the methods of the present invention, a substrate is provided, and the microscale component produced by removing at least a portion of the substrate. The substrate may be removed by etching to produce a set of microscale orifices on the substrate, with the set of orifices positioned around a substrate member having an axis substantially perpendicular to a surface of the substrate. The substrate member substantially spans the cross-sectional depth of the substrate and has a plurality of radial projections. The substrate member and radial projections span the cross-sectional depth of the substrate. Subsequently the radial projections are etched so that they span a portion of the cross-sectional depth of the substrate, e.g., 50% of the cross-sectional depth, or less than 50%, or less than 40%, or less than 30%, or less than 20%, or less than 10%, or less than 5%.

In a further aspect of the invention, a system for delivering a drug to a patient is provided. The system includes an implantable, hydrogel-actuated microvalve according to the present invention; a catheter, with one end of the catheter in communication with the hydrogel-actuated microvalve; a reservoir containing the drug in communication with the second end of the catheter; and a pump capable of delivering the drug from the reservoir through the catheter to the hydrogel-actuated microvalve. The end of the catheter in communication with the microvalve may be positioned intraperitoneally, subcutaneously, or intravascularly in the patient. The pump may be a volatile liquid/bellows pump, an osmotic pump, or an electromechanical pump. The drug reservoir may be located outside the body of the patient. Alternatively, the drug reservoir may be positioned subcutaneously on the patient. The system may further include a flow meter positioned between the reservoir and the microvalve to monitor the flow of the drug. In one embodiment, the system is used to deliver the drug insulin to diabetic patients.

It is yet another aspect of the present invention to provide a hydrogel-mediated device for pulsatile delivery of a hormone. The in vivo, endogenous delivery of hormones occurs by an ultradian, pulsatile method, and it is an object of the present invention to mimic this delivery of hormones in order to regulate certain physiologic states. The hydrogel-mediated device includes a first reservoir that is connected to a source of glucose and to a pH stat; a second reservoir that contains a source of glucose oxidase, a source of the hormone, and a proton sink; and a pH-sensitive hydrogel membrane between the first and second reservoirs. Enzymatic degradation of glucose to gluconate ions and protons results in rhythmic pH cycling of the pH-sensitive hydrogel between a swollen and a collapsed (de-swollen) state, with a concomitant pulsatile delivery of the hormone.

The source of glucose can deliver glucose at a constant concentration of from about 0.1 mM to about 100 mM. Alternatively, the source of glucose delivers glucose at a constant concentration of from about 1.0 mM to about 50 mM. The pH stat maintains the pH of the first reservoir in the range of from about pH 5.5 to about pH 8.0. In another embodiment, the pH stat maintains the pH of the first reservoir in the range of from about pH 6.5 to pH 7.5. Alternatively, the pH stat can maintain the pH of the first reservoir at about pH 7.0.

The source of glucose oxidase can be a gel particle that includes glucose oxidase. The gel particle can include acrylamide. The gel particle optionally may include catalase and/or albumin.

The hormone can be, without limitation, gonadotropin releasing hormone, human growth hormone, prolactin, thyroid stimulating hormone, adrenocorticotropic hormone, luteinizing hormone, follicle stimulating hormone, β-endorphin, melatonin, vasopressin, rennin, parathyroid hormone, pancreatic polypeptide, somatostatin, glucagon, estradiol, progesterone, testosterone, aldosterone, or cortisol. In one embodiment, the hormone is gonadotropin releasing hormone.

The proton sink can include calcium carbonate, magnesium carbonate, potassium carbonate, or sodium carbonate. The proton sink may be in the form of pellets, marbles, or particles. Alternatively, the proton sink may be dissolved in solution. In one embodiment, the proton sink is calcium carbonate.

The pH sensitivity of the hydrogel membrane can result in a volume-decrease at a pH range from about pH 7.4 to about pH 3.5. Alternatively, the volume-decrease can occur at a pH range from about pH 5.5 to about pH 3.5.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference to their entirety. In case of conflict, the present specification, including definitions, will control. In addition, the methods, materials, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4(*a-f*) demonstrates a method for manufacturing a microscale component according to the present invention.

Like reference symbols in the various drawings indicate like elements.

DETAILED DESCRIPTION

Figure 1:
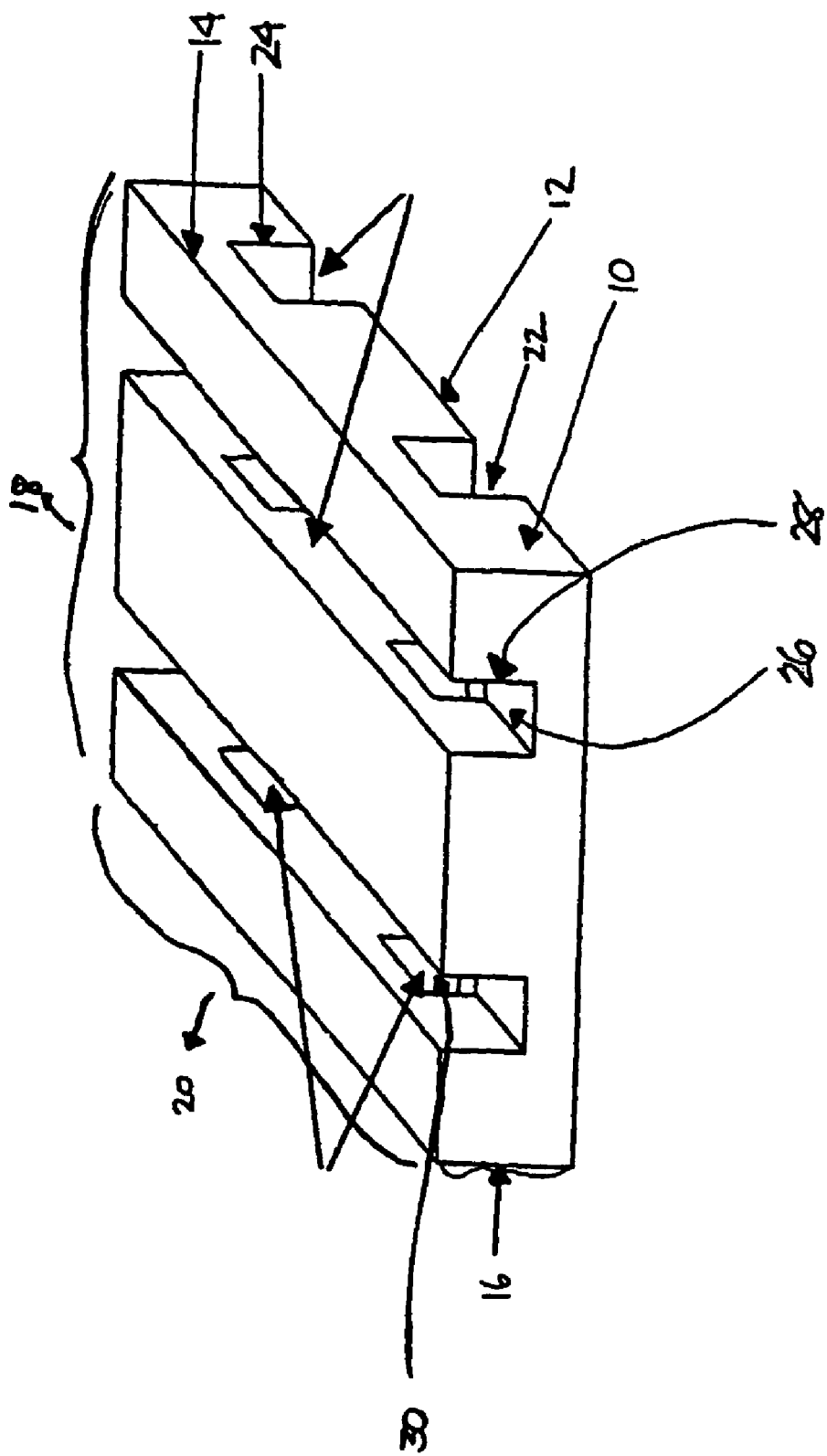
FIG. 1 shows an embodiment of intersecting microscale channels formed by a method of the present invention.

The present invention provides hydrogel compositions, microscale components, and hydrogel-actuated or mediated devices, and methods to manufacture hydrogel microscale components for incorporation into microscale devices. Such microscale devices include, without limitation, implantable drug delivery devices and in-process chemical or fermentation stream monitoring devices. The methods of manufacture are simple and rapid, and allow for integration of one or more microscale components into an overall microscale device.

Hydrogels are physiologically insoluble, three-dimensional, cross-linked polymeric networks. Certain hydrogel compositions are stimulus-sensitive and can undergo reversible volume changes in response to a physical or chemical change, such as a temperature or pH change, or the presence of a chemical compound or biological agent. The stimulus-sensitive hydrogels can directly convert chemical energy into mechanical work, and have been termed "smart" or "intelligent" hydrogels. As used herein, the terms "stimulus-sensitive" or "stimulus-responsive" mean that the hydrogel undergoes a volume change in response to at least one stimulus (e.g., a chemical compound). In the art, the term "stimuli-responsive" or "stimuli-sensitive" is used to refer to hydrogels that similarly undergo a volume change in response to at least one stimulus. Hydrogels that are referred to as "stimuli-responsive" or "stimuli-sensitive" are thus contemplated for use in the present invention.

A number of stimulus-sensitive hydrogel compositions may be used in the methods, components, or devices of the present invention, including hydrogels that respond to physical changes, such as temperature or pressure changes; to chemical changes, such as a pH or ionic strength change; to chemical compounds, including metal ions (for example, $Pb(II)$, $Fe(II)$; $Fe(III)$, $Cr(III)$, $Mn(II)$, $Mg(II)$, $Cu(II)$, $Pb(II)$), lactate, lactic acid, ethanol, ammonia, glycerol, and glucose; and to biological agents, such as toxins, proteins, pathogens, hormones, nucleic acids, antibodies, viruses, and peptides.

The wide range of stimulus-sensitive hydrogel compositions available allows a range of applications for the resultant microscale devices, including chemical or biotechnological process monitoring, physiologic analyte detection, fermentation stream monitoring, medical or clinical testing, and drug delivery. The microscale devices of the present invention also allow the monitoring of numerous analytes in blood, interstitial fluids, and plasma in a minimally invasive and, if required, long-term manner. The methods, devices, and compositions of the present invention are useful in the manufacture of implantable microscale drug delivery devices for controlled drug delivery, including pulsatile, periodic release of hormones. Such controlled drug delivery devices are useful to monitor blood glucose and to deliver insulin responsively in the treatment of diabetes; to deliver the numerous compounds used in the treatment of AIDS; and to deliver a variety of other drugs, including antifungal, antibacterial, contraceptive, chemotherapeutic, steroidal, anti-inflammatory, hormonal, and psychoactive compositions.

The present invention takes particular advantage of the rapid response time of hydrogels at microscale sizes. The response time of a hydrogel volume change is theoretically rapid at microscale sizes because it is proportional to the square of the gel dimension when diffusion is the rate-limiting factor governing swelling. In order to harness the response time efficiently, however, the hydrogel requires adequate exposure to the environment. This goal has been compromised in the past to ensure adequate confinement of a hydrogel component in the overall microscale device. The present invention results in microscale hydrogel components and devices that have both high environmental exposure of the hydrogel and yet adequate structural confinement to ensure component and device integrity.

Microscale Components and Method of Manufacture

One aspect of the present invention is to provide microscale components and methods of manufacturing the same. The microscale components may incorporate hydrogels in, e.g., channels, orifices, openings, etc. to allow the microscale components to function as active microvalves. In one embodiment, a microscale component includes a substrate having a first set of one or more microscale channels on a first surface of the substrate, with the channels of the first set having a depth of more than half of the cross-section depth of the substrate. The microscale component includes a second set of one or more microscale channels on a second surface of the substrate, with the channels of the second set having a depth of more than half of the cross-section depth of the substrate, and the second set in an orientation to the first set to allow the first and second sets to intersect. The microscale component can further include a hydrogel at the intersection of the first and second sets of microscale channels.

In another aspect, a method for making a microscale component is provided. Referring to FIG. 1, a hydrogel microscale component can be formed at the intersection of two sets of microscale channels formed on a substrate. The substrate (10) can be, for example, glass, plastic, silicon, or a transparent mineral. The substrate may be a glass wafer. The substrate has at least two surfaces (12, 14), and a cross-section depth of from about 100 to about 1000 µm (16). The substrate's height and width dimensions (18, 20) can independently range from about 0.5 mm to about 40 mm.

A first set of one or more microscale channels (22) is formed on a first surface of the substrate by removing at least a portion of the substrate. The first set of microscale channels may be parallel to each other. If there is more than one microscale channel, the channels should be spaced a sufficient distance apart to preserve the structural integrity of the substrate between the channels. For example, they may be spaced about 50 µm apart. In one embodiment, they may be spaced from about 100 to about 250 µm apart.

The first set of microscale channels has a depth of more than half of the cross-section depth of the substrate (24), and thus the depth will vary depending on the substrate depth chosen. As one of skill in the art will recognize, the depth of the microscale channel should not be so large as to affect the structural integrity of the substrate. The aspect ratio (width to depth ratio) of the first set of microscale channels can range from about 1:10 to about 10:1. The aspect ratio of the first set of microscale channels alternatively can range from about 1:5 to about 5:1. In one embodiment, the aspect ratio is about 1:3.

A second set of one or more microscale channels (26) is formed on a second surface of the substrate. The second set of microscale channels may be parallel to each other. If there is more than one microscale channel, the channels should be spaced a sufficient distance apart to preserve the structural integrity of the substrate between the channels. For example, they may be spaced about 50 µm apart. In one embodiment, they may be spaced from about 100 to 250 µm apart.

The second set of channels has a depth of more than half of the cross-section depth of the substrate (28) and thus the depth will vary depending on the substrate depth chosen. The depth of the second set of microscale channels need not be the same as the depth of the first set of microscale channels. The aspect ratio (width to depth ratio) of the second set of microscale channels can range from about 1:10 to about 10:1. The aspect ratio of the second set of microscale channels can alternatively range from about 1:5 to about 5:1. In one embodiment, the aspect ratio is about 1:3.

The first and second set of microscale channels can be independently formed by a number of processes, including lithography and deep trench etching.

The second set of one or more microscale channels is positioned in an orientation to the first set of microscale channels to allow the first and second sets to intersect (30). The second set of microscale channels may be positioned in an orientation perpendicular to the first set of microscale channels.

In embodiments where the microscale component includes a hydrogel, a liquid polymerizable mixture is introduced into the first and second sets of microscale channels. The liquid polymerizable mixture may include one or more comonomers, one or more cross-linkers, and optionally a buffer and/or a solvent. The liquid polymerizable mixture also may include a responsive composition that contributes to the desired physical, chemical, or biological responsiveness of the resultant hydrogel after polymerization.

Residual polymerized liquid polymerizable mixture is removed from the first and second sets of microscale channels to provide the microscale component with a hydrogel at the intersection of the first and second sets. See FIG. 2. The residual unreacted mixture may be removed by flushing the first and second sets of microscale channels with an appropriate buffer or with deionized water. An appropriate buffer may be the same buffer used, if any, for the preparation of the liquid polymerizable mixture, or it may be a different buffer. For example, in medical devices, phosphate buffered saline (0.015 M, pH 7.4) may be used.

Figure 3:
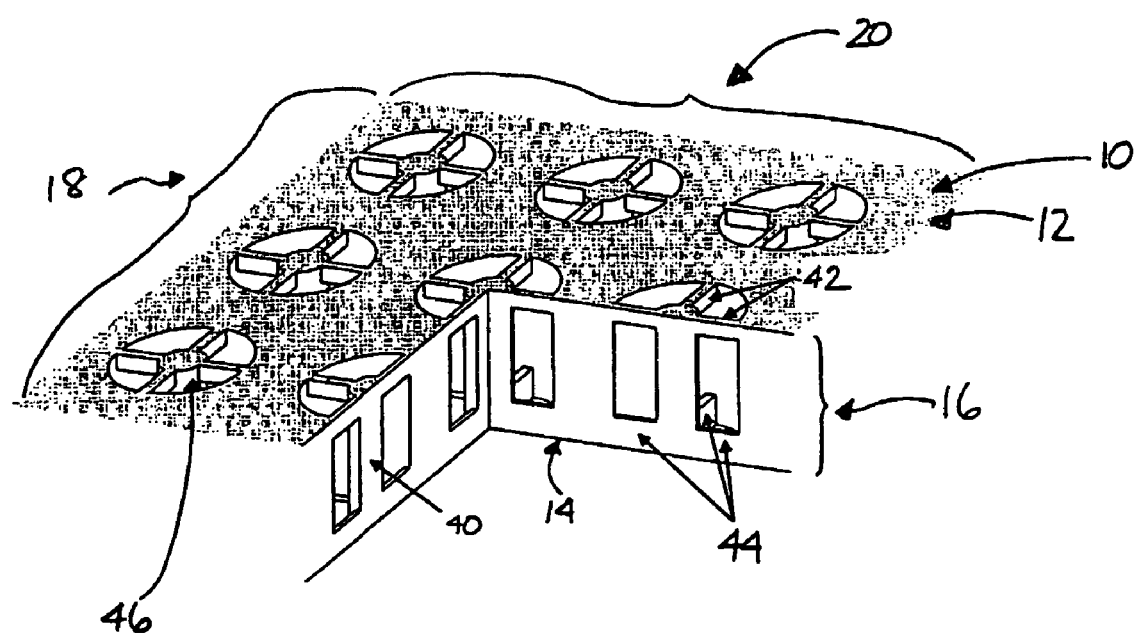
FIG. 3 shows an embodiment of a microscale component according to the present invention.

In another embodiment, referring to FIG. 3, a microscale component includes a substrate (10) having a substrate member (40) that substantially spans the cross-sectional depth (16) of the substrate, e.g., spans more than 50%, or more than 60%, or more than 75%, or more than 85%, or more than 95% of the cross-sectional depth of the substrate. The substrate member can be any shape, e.g., columnar, rectangular, cylindrical, or irregular in shape. The substrate member has an axis substantially perpendicular to a surface of the substrate. The substrate member can be perpendicular to the surface of the substrate. The substrate member has a plurality of radial projections (42, 44) that span a portion of the cross-sectional depth of the substrate. For example, the substrate member may have 2, 4, 6, 8, or more radial projections. The radial projections may extend from either end of the substrate member, or from both ends (42, 44). A hydrogel may be positioned adjacent to the substrate member and radial projections in the microscale component, allowing the hydrogel to be tethered to one or more of the substrate member and radial projections. The microscale component structure thus prevents the hydrogel from escaping (e.g., traps the hydrogel) when it is in an unswollen state.

Referring to FIG. 3 and FIG. 4 (a-f), a method for manufacturing the microscale component is shown. The microscale component can be formed with an array of orifices having an internal structure designed to confine a hydrogel while still allowing the hydrogel to control the flow across a substrate. The substrate (10) can be, for example, glass, plastic, silicon, or a transparent mineral. The substrate may be a glass wafer or a silicon wafer. The substrate has at least two surfaces (12, 14), and a cross-section depth of from about 100 to about 1000 µm (16). The substrate's height and width dimensions (18, 20) can independently range from about 0.5 mm to about 40 mm. The substrate may have a deposit on it. The deposit may facilitate patterning and etching of the substrate. The deposit may be a nitride deposition, e.g., a 2 μm LPCVD (low pressure chemical vapor deposition) low stress nitride deposition.

The microscale component is produced by removing at least a portion of the substrate to leave a substrate member (40) having a plurality of radial projections (42, 44). There may be more than one substrate member. If there is more than one substrate member, they should be placed sufficiently apart to preserve the structural integrity of the substrate. The substrate member has an axis substantially perpendicular to a first surface of said substrate and substantially spans the cross-sectional depth (16) of the substrate. The plurality of radial projections span a portion of the cross-sectional depth of the substrate.

The substrate may be removed by a number of processes, such as etching and lithography. If there is a deposit on the substrate, it may be patterned to facilitate the removal of the substrate. The substrate may be etched, e.g., in KOH, on a first surface to produce a substrate of the desired cross-sectional depth (16), e.g., a 100 μm substrate (FIG. 4b). The substrate may then be etched on a second surface to produce a set of microscale orifices (46), wherein the set of orifices is positioned around the substrate member. The orifices are separated by the plurality of radial projections of the substrate member (FIG. 4c, 4d). The radial projections are subsequently etched so that they span a portion of the cross-sectional depth of the substrate (FIG. 4e). The radial projections so etched may be triangular in shape to form tethers, e.g., triangular tethers. The substrate may be etched further on the first surface to produce a plurality of radial projections, which span a portion of the cross-sectional depth of the substrate (FIG. 4f). The plurality of radial projections may be triangular in shape and form tethers.

A liquid polymerizable mixture may be introduced into the microscale component and polymerized to result in a hydrogel positioned adjacent to the substrate member and radial projections. The hydrogel is confined, e.g., tethered, within the microscale component, while still controlling the flow. The small dimension of the hydrogel-confining microscale component permits the achievement of shorter response times to the pre-determined stimulus. The microscale component can function as an active microvalve and can be designed to control a wide range of flow rates by adjusting the diameter and number of orifices in the substrate.

Hydrogel Compositions

Hydrogels for use in the present invention are three-dimensional networks capable of rapidly and reversibly undergoing a volume phase transition in response to a predetermined stimulus. The hydrogel microscale components demonstrate not only the ability to expand and to contract, but also the ability to couple this volume responsiveness in a defined manner to a predetermined stimulus in a medium contacting the hydrogel component.

Any number of known comonomers and crosslinkers may be used to prepare a hydrogel in the methods of the present invention. For example, representative comonomers and crosslinkers are set forth in PCT publication WO 01/07506. Typically, one or more comonomers will be employed, with one or more comonomer-derivatives acting as cross-linkers. The comonomers, cross-linkers, and responsive composition may be derivatized, e.g, with ethylene glycol, polyvinyl alcohol, etc., and, as one of skill will recognize, are chosen to provide a polymer gel with the physical and chemical properties desired for the hydrogel component and device.

In one embodiment, acrylamide may be used as the comonomer, with N,N'-methylene bis-acrylamide as the cross-linker, to result in polyacrylamide hydrogels. Drug-loaded polyacrylamide hydrogels have been studied in drug-delivery systems, both in vivo and in vitro. Polyacrylamide hydrogels also may be modified with ethylene glycol, polyvinylalcohol, chitosan, and N,N-dimethylaminopropylacrylamide. Acrylamide may be used in a concentration range of about 60-95 mol %. N,N'-methylene bis-acrylamide may be used in a concentration range of about 0.05-2 mol %. The liquid polymerizable mixture may be pre-loaded with polymerization initiators TEMED (N,N,N',N'-tetramethylethylenediamine) and APS (ammonium persulfate) or with a UV polymerization initiator (e.g., azo-bis-isobutyronitrile) when it is introduced into the channels.

The liquid polymerizable mixture also may include a responsive composition to contribute the desired responsiveness of the polymerized hydrogel to the physical, chemical, or biological parameter in the medium. The responsive composition may or may not be crosslinked to the hydrogel after polymerization. For example, 3-methylacrylamidophenylboronic acid and Concavalin A can render a hydrogel glucose-sensitive.

The liquid polymerizable mixture can include optional additives, such as dyes, surface active agents, viscosity modifiers, thixotropic agents, pigments, flow agents, thickeners, plasticizers, and other additives to modify a physical property of the liquid polymerizable mixture or the hydrogel. As one of skill in the art will recognize, the amount of additive required will vary on the intended purpose and the hydrogel composition.

Other hydrogel compositions contemplated for use in the present invention include poly(acryloyl-L-proline methyl ester) hydrogels; poly(n-isopropylacrylamide) hydrogels; lactitol poly(ether polyol) hydrogels (known as LPEP); poly (hydroyethyl methacrylate) hydrogels (known as PHEMA); vinylpyrrolidinone-allylglucose (known as VP/AG); poly(2-hydroxyethyl methacrylate-co-N,N-dimethylaminoethyl methacrylate) hydrogels (known as poly(HEMA-co-DMAEMA)); poly(N-isopropylacrylamide-co-methacrylic acid) (known as NIPA/MAA); and poly(n-isopropylacrylamide-co-acrylic acid).

If the hydrogel microscale component is used in an implantable medical device, the hydrogel is preferably biocompatible in order to minimize any inflammatory or toxic responses. Alternatively, the medical device may be isolated from direct contact with the blood, plasma, interstitial fluids, or tissue of the patient through the use of molecular weight cut-off membranes, films, and the like. Such a system would prevent patient-exposure to any toxic hydrogel-derived compounds, but ensure adequate exposure of the hydrogel component to the medium.

Buffers for use in the method of the present invention should be unreactive to the polymerization step, and if the device is used in an implantable medical device, should be biocompatible. Any number of known buffers may be used, including, without limitation, phosphate buffered saline, phosphate, HEPES, and TRIS buffers. Any solvents should also not be reactive to polymerization, should be biocompatible if necessary, and should preferably have a low molecular weight and boiling point. Solvents contemplated for use in the present invention include ethanol, methanol, ethers, ketones (e.g., acetone), dioxane, DMSO, water, and aliphatic and aromatic hydrocarbons.

The liquid polymerizable mixture may be polymerized in a number of ways. A polymerization initiator may be added to the liquid polymerizable mixture so that polymerization commences as the liquid polymerizable mixture is introduced into the microscale channels. For example, N,N,N',N'-tetramethylethylenediamine (TEMED) and ammonium persulfate (APS) may be added to an acrylamide/bis-acrylamide liquid polymerizable mixture before introduction into the microscale channels. Alternatively, polymerization can occur after introduction of the liquid polymerizable mixture into the microscale channels. For example, TEMED/APS may be added after introduction of the liquid polymerizable mixture into the microscale channels. Alternatively, the polymerization initiator may be a UV-sensitive (e.g., 250-450 nm) photoinitiator. After introduction of the liquid polymerizable liquid, cross-linking can be accomplished by shining the appropriate wavelength of light (e.g., with an optical waveguide) over the liquid polymerizable mixture. Azo-bis-isobutyronitrile or 2,2-dimethoxy-2-phenyl acetophenone may be used as the photoinitiator for UV-photoinitiation. Other suitable photoinitiators are set forth in PCT publication WO 01/07506.

The time frame for polymerization will vary depending on the particular liquid polymerizable mixture chosen and the method of polymerization. The hydrogel may polymerize in the range from about 1 minute to about 1 hour. The hydrogel alternatively may polymerize in the range from about 1 minute to about 10 minutes.

The hydrogel microscale components of the present invention can function as active microvalves in response to the predetermined stimulus. The predetermined stimulus may be a physical change, a chemical change, a chemical compound, or a biological agent. The physical change can be a temperature change, an electric field change, a change in light absorption, a change in light emission, a magnetic field change, and a pressure change. Alternatively, the predetermined stimulus may be a chemical change in the medium contacting the hydrogel. The chemical change may be a pH change or an ionic strength change. For example, PCT publication WO 01/07506 describes pH sensitive hydrogels for use in microscale devices.

One particular embodiment of a pH sensitive hydrogel includes 2-(dimethylamino)ethyl methacrylate as a cross-linker, 2-hydroxyethyl methacrylate as a comonomer, ethylene glycol dimethyacrylate, and 2,2-dimethoxy-2-phenyl acetophenone as a photoinitiator. Another example of a pH sensitive hydrogel is poly(N-isopropyl acrylamide-co-methacrylic acid) (NIPA/MAA), which swells with increasing pH.

The predetermined stimulus may also be the presence or absence of a chemical compound in the medium contacting the hydrogel. For example, the chemical compound may be any one of various metal ions (e.g, Cu(II), Fe(II), Fe(III), Mn(II), Mg(II), Cr(III)), lactate, ammonia, glycerol, glucose, ethanol, or lactic acid. The incorporation of a responsive composition, including, for example, a biomolecule or other molecule that binds the chemical compound of interest, can contribute to the volume-responsiveness of a hydrogel to a particular compound.

Figure 2:
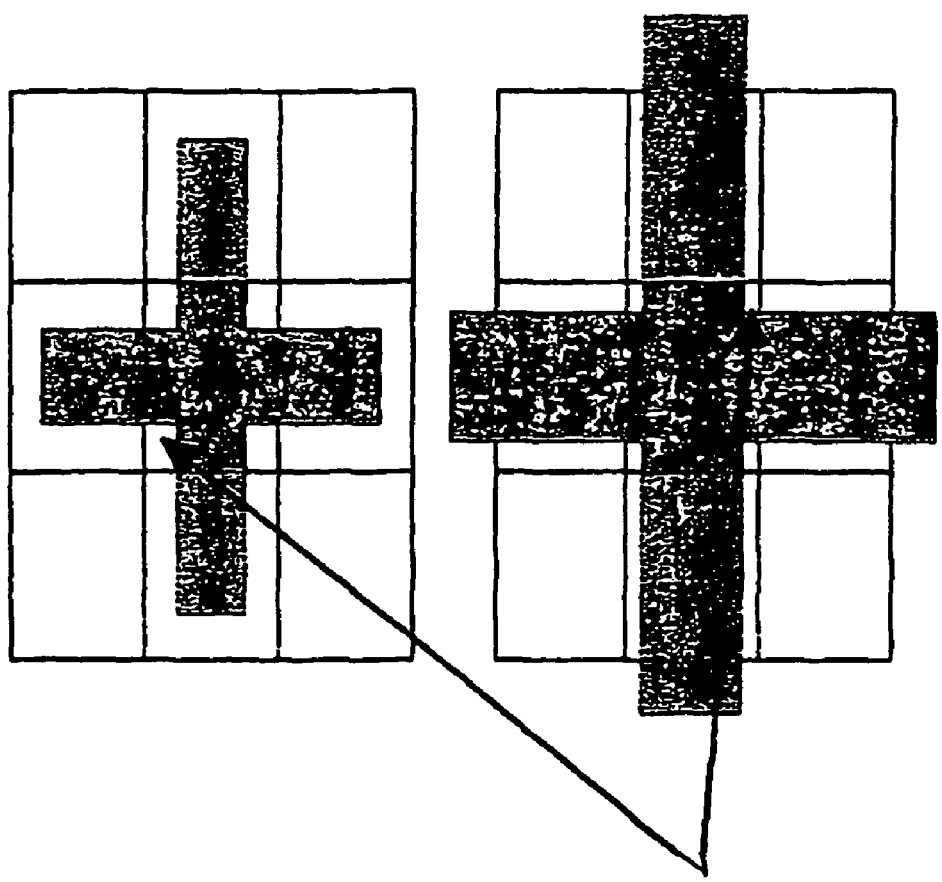
FIG. 2 shows an embodiment of a hydrogel in a microscale component. The dark area on the figure corresponds to the hydrogel.
Figure 5:
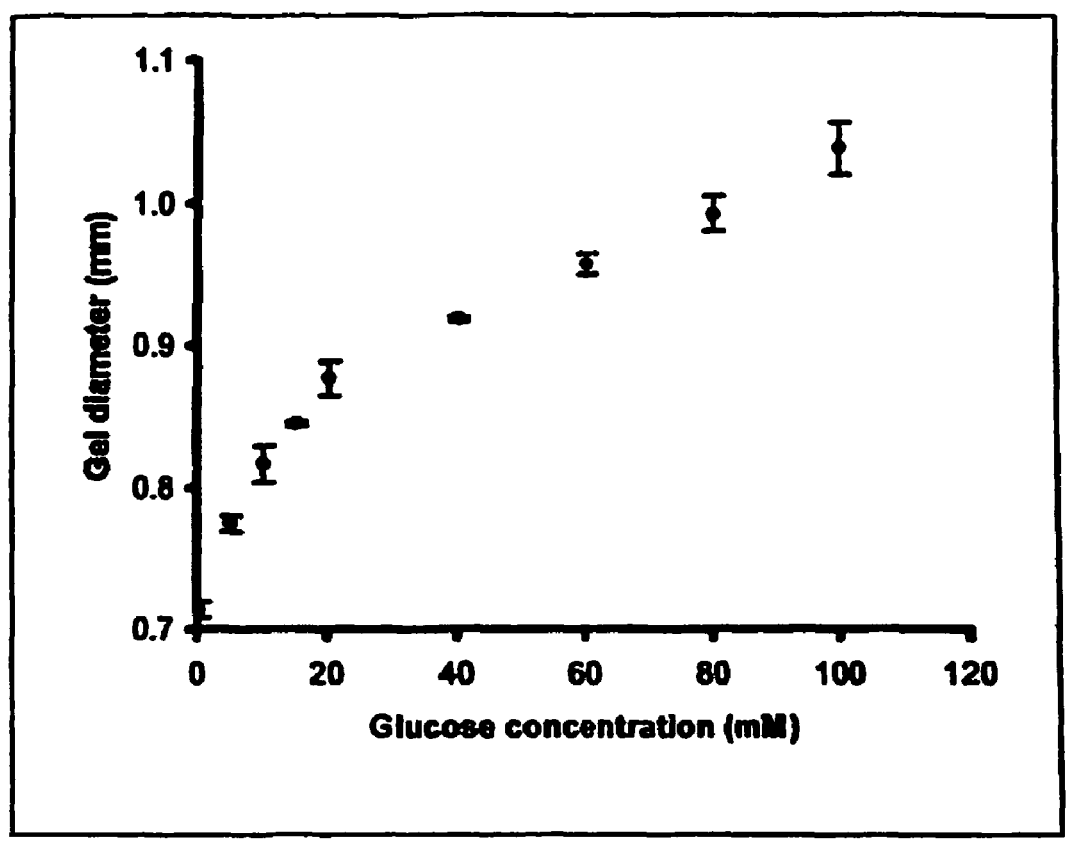
FIG. 5 demonstrates the volume response to glucose of an acrylamide/bis-acrylamide hydrogel containing 3-methylacrylamidophenylboronic acid.
Figure 6:
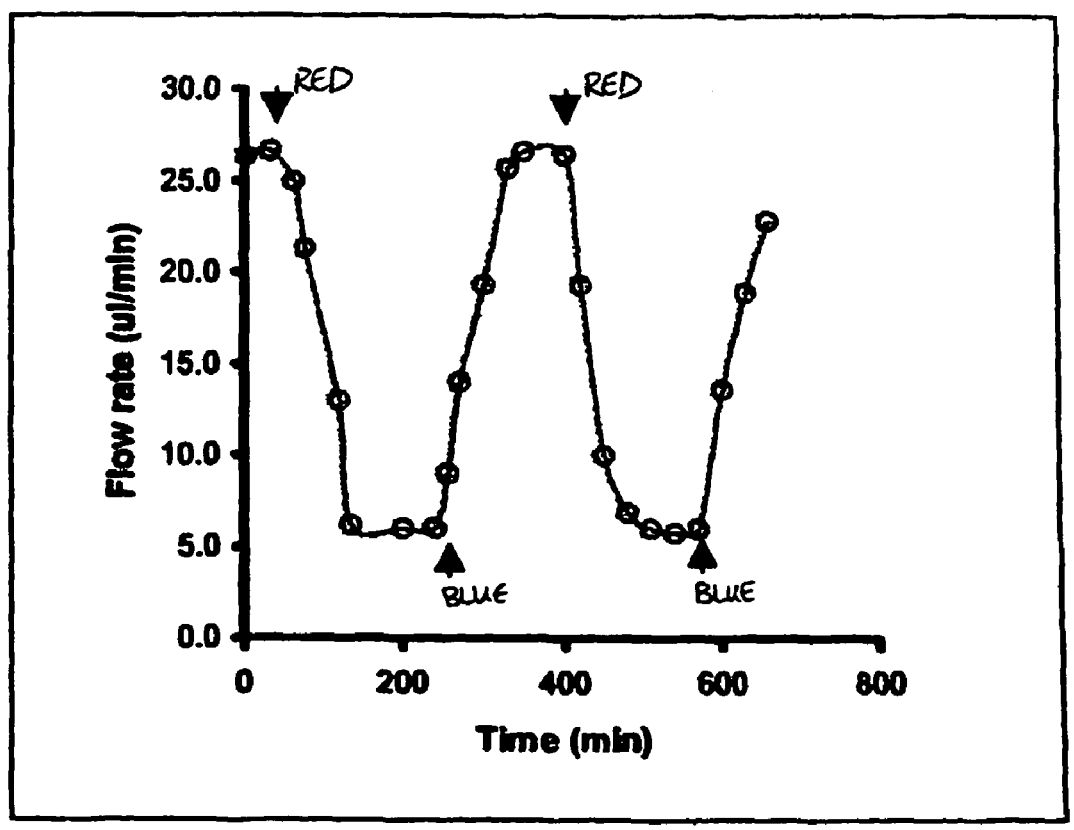
FIG. 6 demonstrates the flow rate through a hydrogel microscale component (an acrylamide/bis-acrylamide hydrogel containing 3-methylacrylamidophenylboronic acid) in response to the presence and absence of glucose.

Acrylamidophenylboronic acid and its derivatives, such as 3-methyl acrylamidophenylboronic acid, can cause hydrogels to swell in response to the presence of glucose. For example, in one embodiment of a glucose-sensitive hydrogel microscale component of the present invention, about 81.5 mol % acrylamide comonomer, 0.1% N,N'-methylenebisacrylamide cross-linker, and 18.4 mol % 3-methylacrylamidophenylboronic acid were suspended in 0.015 M, pH 7.4 phosphate buffered saline (PBS) to form the liquid polymerizable mixture. TEMED/APS was added as a polymerization initiator. The liquid polymerizable mixture was introduced into the microscale channels of the microscale component described previously and polymerized (e.g., with UV light) to produce a hydrogel microscale component. As shown in FIG. 2, FIG. 5, and FIG. 6, the glucose-sensitive hydrogel microscale component functioned as an active microvalve in response to glucose, effectively shutting off flow at high glucose concentrations when it was swollen, while allowing flow at lower glucose concentrations when it was shrunken.

The swelling behavior of a phenylboronic acid (PBA)-containing hydrogel is due to the effect of glucose and other saccharides containing planar diols on the ionization of PBAs. Phenylboronic acids (PBAs) moieties exist in charged and uncharged states according to a typical acid-base equilibrium. In saline solutions, the fraction of PBA groups ionized, $\alpha$, is related to pH through the standard Henderson-Hasselbach relation:

$$pH = pK_0 + \log_{10}\frac{\alpha}{1-\alpha}$$

PBA-containing hydrogels with pH well below $pK_0$ are not ionized, and therefore are not swollen.

Molecules containing planar diols, such as saccharides, complex with PBAs and stabilize the charged, basic form. This amounts to replacing $pK_0$ in the previous equation with pKa, where:

$$pKa = pK_0 - \log_{10}(1+[sacc]/K_f)$$

and where [sacc] is the molar concentration of added saccharide and $K_f$ is the "formation constant," related to the binding affinity of saccharide to the PBA moiety. An increase in saccharide concentration lowers the pKa and increases ionization of the gel.

Figure 7:
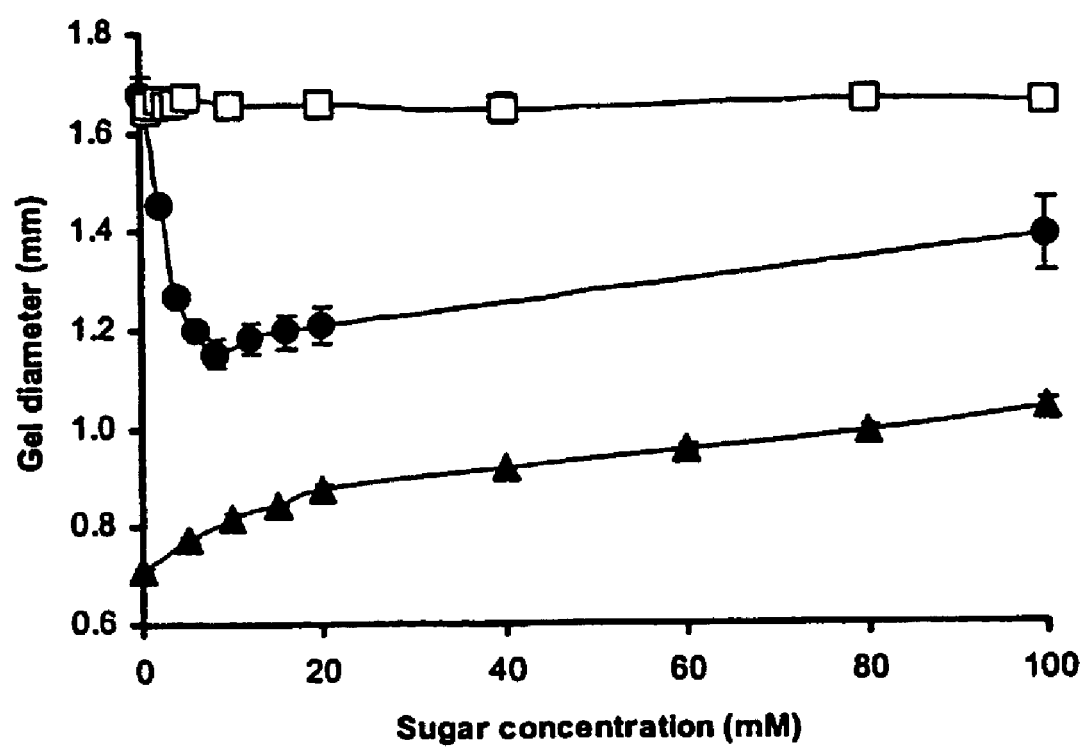
FIG. 7 demonstrates the modes of swelling of a phenylboronic acid gel at pH 7.4 and pH 10 in the presence of fructose or glucose. The open squares demonstrate the swelling behavior of a pH 10 PBA gel in the presence of fructose. The filled circles demonstrate the swelling behavior of a pH 10 PBA gel in the presence of glucose. The filled triangles demonstrate the swelling behavior of a pH 7.4 PBA gel in the presence of glucose.

An example of this phenomenon is shown in FIG. 7, demonstrating the swelling behavior for a hydrogel containing 20% methacrylamidophenylboronic acid (MPBA) and 80% acrylamide. The $pK_0$ of MPBA is 8.8, so when $pH \ll pK_0$ (e.g., pH 7.4), and in the absence of glucose, the hydrogel is uncharged and not swollen. With added glucose, the effective pKa shifts down towards the ambient pH, and the hydrogel ionizes and swells.

If $pH > pK_0$ of PBA (e.g., pH 10), then the hydrogel swelling behavior depends on the particular saccharide. For example, hydrogel swelling is virtually unaffected by fructose at pH 10, since the hydrogel is charged whether or not fructose has been added. However, charged PBA-based hydrogels at pH 10 initially shrink with addition of glucose, and then reswell at higher glucose concentrations. While not being bound by any theory, such effects may be due to reversible crosslinks formed as 1:2 complexes between a glucose molecule and two charged PBA sidechains. At high glucose concentrations, these 1:2 complexes are broken and replaced by two 1:1 complexes, allowing reswelling. Fructose, on the other hand, does not contain enough planar diols to enable this reversible crosslinking to occur.

Figure 8:
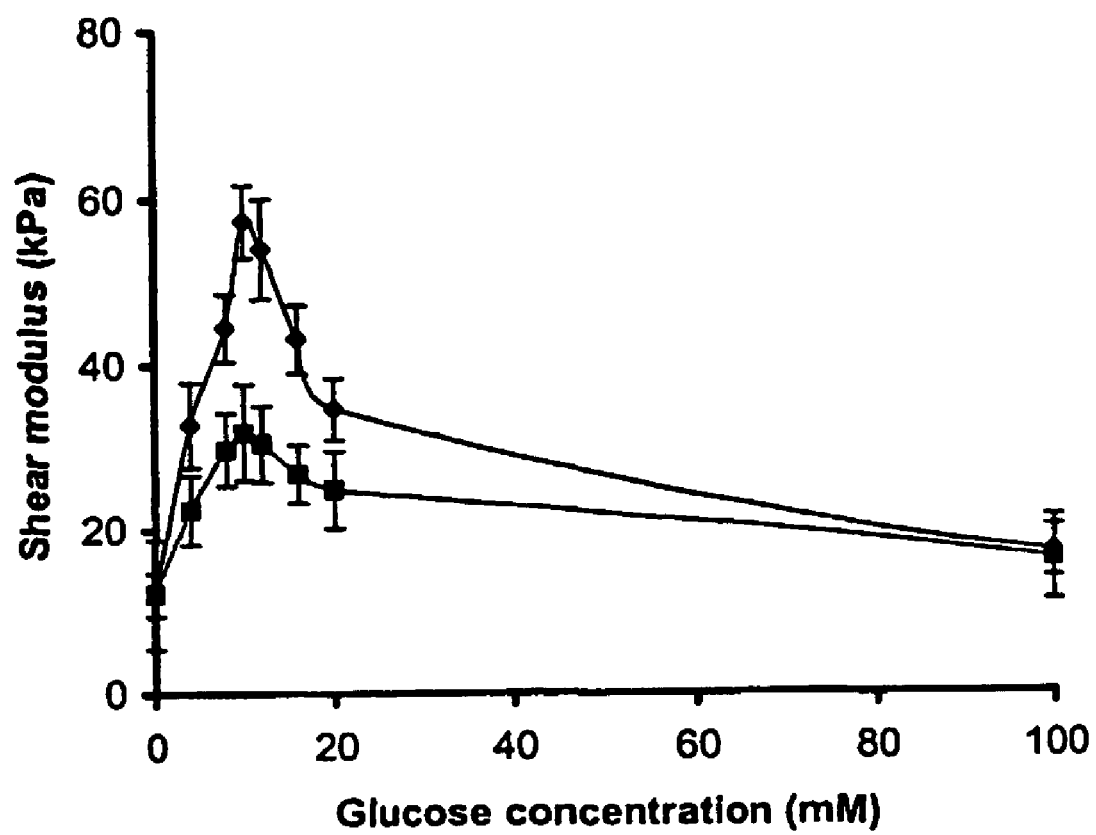
FIG. 8 demonstrates the shear modulus measurement of a glucose-responsive hydrogel, with the filled squares indicating the calculated modulus based on the volume change of the hydrogel, and with the filled diamonds indicating the measured modulus values.

Evidence that glucose-induced crosslinking mediates the swelling response at pH 10 is provided by shear modulus measurements, as shown in FIG. 8. This graph shows that shear modulus peaks exactly where swelling reaches its minimum and shear modulus changes are not solely accounted for by volume change. These two observations support an initial increase and subsequent decrease in crosslink density with increasing glucose concentration. Glucose-mediated swelling and shrinking are thus both potential means of converting changes in glucose concentration into the opening and shutting of microvalves.

Another useful responsive composition for use in the hydrogels of the present invention is 3-acrylamido-4-nitrobenzeneboronic acid. While not being bound by any theory, it is believed that 3-acrylamido-4-nitrobenzeneboronic acid will have an altered pKa of the phenylboronic acid side chain at neutral pH to result in shrinkage (deswelling) of a hydrogel in response to the presence of glucose.

The concentration of 3-methylacrylamidophenylboronic acid or 3-acrylamido-4-nitrobenzeneboronic acid in a glucose-sensitive liquid polymerizable mixture will vary depending on the nature of the comonomer and crosslinkers used and the end-use contemplated for the hydrogel component, but will generally range from 1 mol % to about 30 mol %. The concentration of 3-methylacrylamidophenylboronic acid or 3-acrylamido-4-nitrobenzeneboronic acid can range alternatively from about 1 mol % to about 25 mol %. The concentration of 3-methylacrylamidophenylboronic acid or 3-acrylamido-4-nitrobenzeneboronic acid can range alternatively from about 1 mol % to about 10 mol %.

In other embodiments, the predetermined stimulus to which the hydrogel is responsive may be a biological agent in the medium contacting the polymer gel. The biological agent may be a toxin, a pathogen, a protein, an antibody, an antigen, a virus, a peptide, and a nucleic acid. The incorporation of a suitable biomolecule as the responsive composition into the hydrogel may allow the hydrogel to be volume-responsive to a particular biological agent. For example, receptors, proteins, antibodies, and antibody-fragments that have affinity or specificity for a particular biological agent and that contribute to a volume-responsive effect may be incorporated into the hydrogel microscale component.

Microscale Devices

The hydrogel microscale components may be incorporated in an integrated device that contains other conventional or hydrogel microscale components. For example, the hydrogel microscale components may be incorporated in in-process chemical and fermentation stream monitoring devices. Since the hydrogel microscale components function as active valves in response to a predetermined stimulus, the components can effectively couple fluid flow with the concentration of a particular analyte in the process-stream.

For fermentation stream monitoring, hydrogel components that are volume-responsive to ammonia, glucose, lactate, lactic acid, and ethanol are useful. In one embodiment, the hydrogel components can function as active microvalves in response to glucose in a fermentation stream. The active microvalve can include, for example, a glucose-sensitive hydrogel composition that increases volume upon exposure to glucose. Such a glucose-sensitive hydrogel composition, for example, can include 3-methylacrylamidophenylboronic acid as the responsive composition, acrylamide as a comonomer, and N,N'-methylenebisacrylamide as a cross-linker. When glucose concentrations are adequate for fermentation, the hydrogel component acts as an active microvalve by closing (e.g. swelling), thereby cutting off the flow of glucose to the medium. As glucose concentrations decrease, the hydrogel component can de-swell, and glucose is again delivered to the medium.

The hydrogel microscale components of the present invention also may be incorporated into implantable medical devices for physiologic analyte monitoring and/or drug delivery. For example, the hydrogel microscale components can be incorporated into catheters.

A diabetic glucose-monitoring system coupled with controlled insulin delivery represents another embodiment of an implantable medical device contemplated by the present invention. In such a system, a glucose-sensitive hydrogel component can be in communication with a microscale pump, reservoir, or source that is capable of delivering insulin. The implantable medical device can include a drug reservoir that is in communication with or is capable of delivering a drug, e.g., insulin, to the microscale component. For example, the drug reservoir can communicate with the microscale component through a catheter, e.g, a catheter implanted subcutaneously, intraperitoneally, or intravascularly. The implantable device can further include a pump to deliver the drug from the drug reservoir to the microscale component. The pump may be a volatile liquid/bellows pump, an electromechanical pump, or an osmotic pump.

It is another object of the invention to provide an implantable microscale system for drug delivery to a patient. The system includes a microscale component according to the present invention; a catheter, with one end of the catheter in communication with the microscale component; a drug reservoir in communication with the second end of the catheter; and a pump capable of delivering the drug (e.g., insulin) from the reservoir through the catheter to the microscale device. The end of the catheter in communication with the microscale component may be positioned intraperitoneally, subcutaneously, or intravascularly in the patient. The pump may be a volatile liquid/bellows pump, an electromechanical pump, or an osmotic pump.

Hydrogel-Actuated Devices

Figure 9:
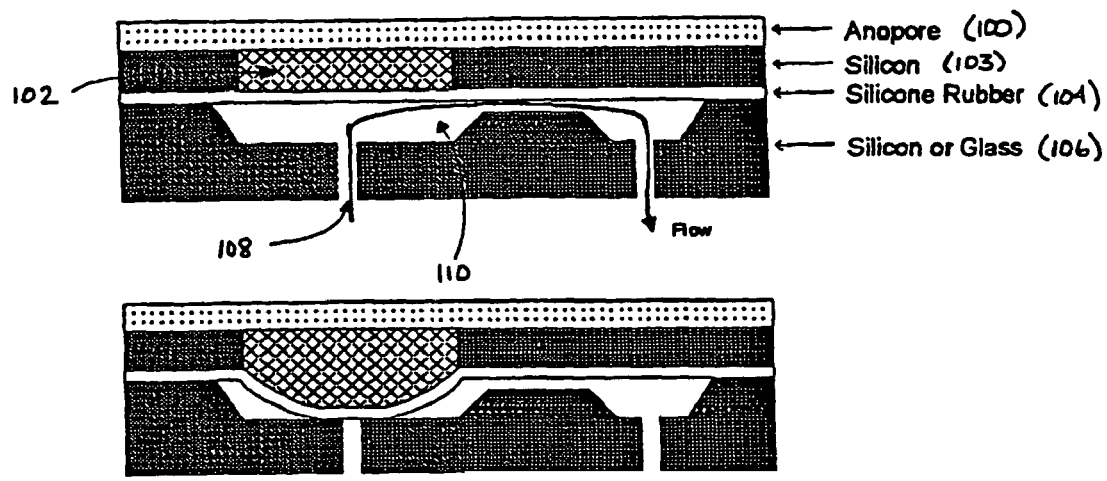
FIG. 9 shows an embodiment of a hydrogel-actuated microvalve.

The present invention takes particular advantage of the fact that responsive hydrogels can efficiently convert chemical energy into mechanical work. One embodiment of a hydrogel-actuated device, a hydrogel-actuated microvalve, is represented in FIG. 9. A first substrate (100) is provided. The first substrate is permeable to a predetermined chemical compound, e.g., glucose. The first substrate can include a porous plate diffusion barrier. Vycor® glass (Corning 7930), Anapore® aluminum oxide, or any other material that can provide homogenous pores in the range of about 10 nm to about 50 μm can be used. The pores should allow the passage of small molecules such as water and buffer components and also the predetermined chemical compound. The first substrate can have a thickness of, for example, from about 50 to about 1000 μm. The first substrate should be resistant to deformation. While not bound by any theory, the first substrate should not relieve the pressure that results from the swelling of the hydrogel; the pressure should instead be transferred to the second substrate to result in deformation of the second substrate. See FIG. 14. The first permeable substrate provides mechanical support for the hydrogel and prevents its escape from the device, while allowing adequate surface exposure of the hydrogel to the medium.

Adjacent to the first permeable substrate is a volume-responsive hydrogel (102). The volume responsive hydrogel may be trapped in a cavity drilled mechanically (e.g., ultrasonic milling) or etched chemically (e.g., HF 10%) in the first substrate. Alternatively, the hydrogel may be formed in a cavity of an optional support substrate (103) (e.g., silicon or glass) positioned between the first permeable substrate and the second deformable substrate.

The volume-responsive hydrogel is capable of undergoing a volume change in response to the predetermined chemical compound to which the first substrate is permeable. The volume responsive hydrogel can include any of the hydrogel compositions described previously, provided that it demonstrates a volume change (either volume increase or volume decrease) upon exposure to a predetermined chemical compound. For example, the hydrogel can be a glucose sensitive hydrogel that swells upon exposure to glucose; such a hydrogel may include, for example, 3-methacrylamidophenylboronic acid as a responsive composition. Alternatively, the hydrogel may shrink upon exposure to glucose; such a hydrogel may include, for example, 3-acrylamido-4-nitrobenzeneboronic acid.

A second substrate (104) is adjacent to the volume-responsive hydrogel. The second substrate is deformable in response to the volume change of the hydrogel. The second substrate can deform by deflection towards or away from the third substrate. The deflection can range from about 10 to about 500 µm. The second substrate should be biocompatible and/or pharmaceutically acceptable. The second substrate can be any reversibly deformable elastomer. For example, the second substrate can be a low modulus silicone, neoprene, or isoprene rubber. If a low modulus silicone rubber membrane is used, it may be produced by spin-coating silicone rubber on a silicon wafer. The silicon wafer may be removed entirely or in selective regions by deep etching or base (KOH) etching.

The third substrate (106) includes an orifice (108). The opening and closing of the orifice regulates fluid flow in the microvalve. When the orifice is open, fluid can flow through the device (e.g., through channels (110) machined in the device). When the hydrogel undergoes a volume increase in response to the predetermined chemical compound, the second substrate deforms by deflection toward the third substrate, resulting in at least a partial sealing of the orifice in the third substrate, and affecting fluid flow. Fluid flow may be reduced in the range from about 10% to about 100% upon the deflection of the second substrate. The third substrate can be manufactured from any material that provides the required structural stability and ability to machine channels and inlet orifices. The third substrate is preferably silicon or glass.

The orifice controls fluid access to a channel (110) disposed between the third and the second substrates. The channel may be sized to fix fluid flow when the orifice is open to a predetermined value. For example, the channel may be sized to permit a required dosing regimen in a drug delivery device.

The response time of the microvalve will depend on, without limitation, the thickness and permeability of the first permeable substrate, the exposure of the hydrogel, the hydrogel composition, the thickness of the hydrogel, the deformability of the second substrate, and the gap between the second substrate and the fluid entry orifice in the third substrate. The response time can range from about 10 sec. to about 1 hour. The response time will preferably range from about 10 sec. to about 10 mins.

The substrates can be manufactured separately and then assembled. The overall assembly of the microvalve can be performed using various adhesives, including UV-curable adhesives. The assembly can be performed under a light microscope.

Figure 10:
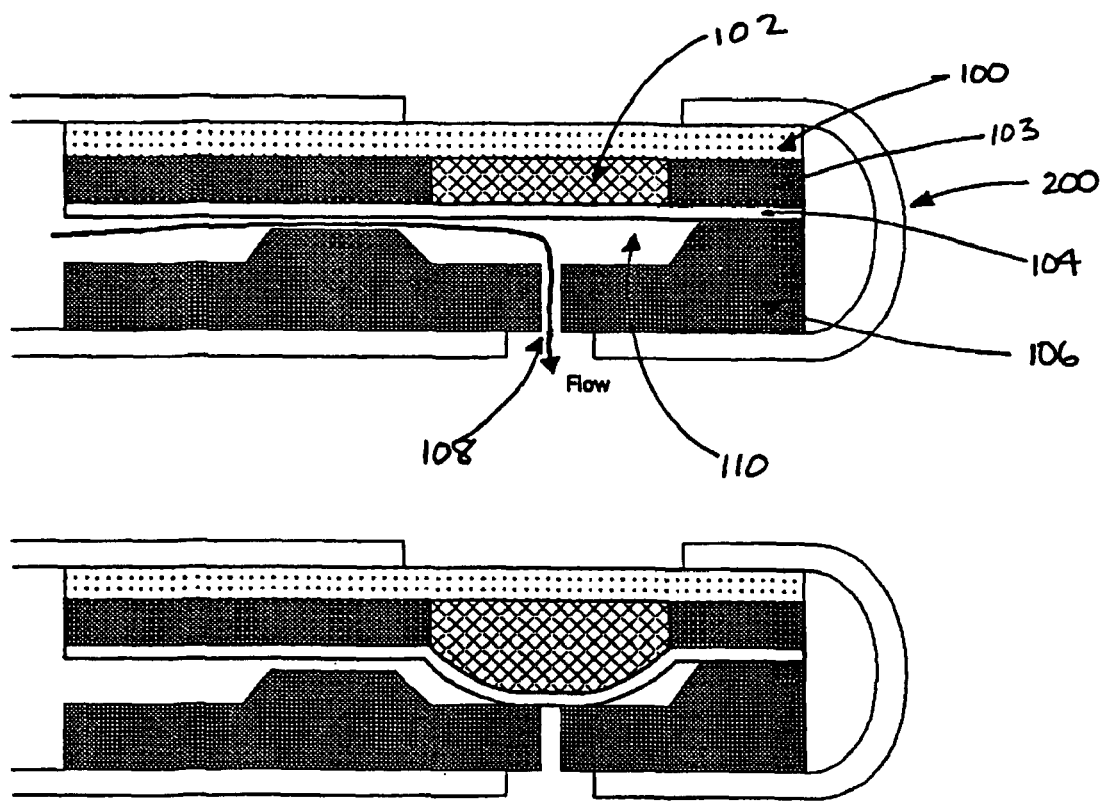
FIG. 10 shows a catheter that includes a hydrogel actuated microvalve according to the present invention.

The implantable, hydrogel-actuated microvalves may be included in catheters to regulate fluid flow through the catheter. See FIG. 10. The catheter (200) may be implanted subcutaneously, intraperitoneally, or intravascularly.

Figure 11:
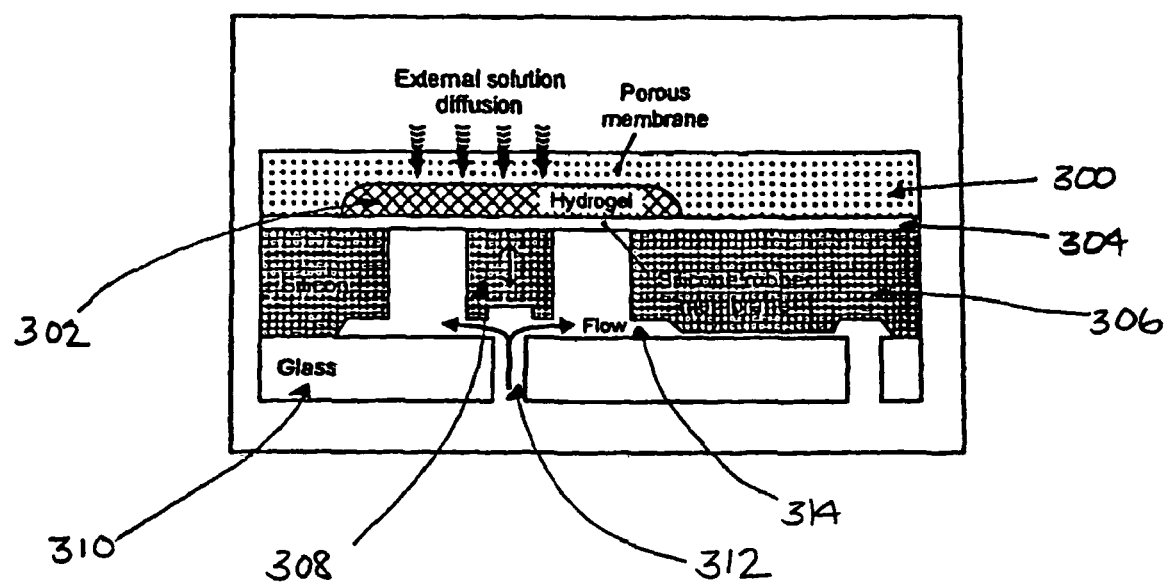
FIG. 11 shows an embodiment of a hydrogel-actuated microvalve where a member is used to seal an orifice to control fluid flow.

Another embodiment of a hydrogel-actuated microvalve is shown in FIG. 11. A first substrate (300) is provided. The first substrate is permeable to a predetermined chemical compound, e.g., glucose. The first substrate can include a porous plate diffusion barrier. Vycor® glass (Corning 7930), Anapore® aluminum oxide, or any other material that can provide homogenous pores in the range from about 10 nm to about 50 µm can be used. The pores should allow the passage of small molecules such as water and buffer components and also the predetermined chemical compound. The first substrate can have a thickness of, for example, from about 50 to about 1000 µm. The first substrate should be resistant to deformation. While not bound by any theory, the first substrate should not relieve the pressure that results from the swelling of the hydrogel; the pressure should instead be transferred to the second substrate to result in deformation of the second substrate. The first permeable substrate provides mechanical support for the hydrogel and prevents its escape from the device, while allowing adequate surface exposure of the hydrogel to the medium.

Adjacent to the first permeable substrate is a volume-responsive hydrogel (302). The volume responsive hydrogel may be trapped in a cavity drilled mechanically (e.g., ultrasonic milling) or etched chemically (e.g., HF 10%) in the first substrate. Alternatively, the hydrogel may be formed in a cavity of an optional support substrate (303) (e.g., silicon or glass) positioned between the first permeable substrate and the second deformable substrate.

The volume-responsive hydrogel is capable of undergoing a volume change in response to the predetermined chemical compound to which the first substrate is permeable. The volume responsive hydrogel can include any of the hydrogel compositions described previously, provided that it demonstrates a volume change (either volume increase or volume decrease) upon exposure to a predetermined chemical compound. For example, the hydrogel can be a glucose sensitive hydrogel that swells upon exposure to glucose; such a hydrogel may include, for example, 3-methacrylamidophenylboronic acid as a responsive composition. Alternatively, the hydrogel may shrink upon exposure to glucose; such a hydrogel may include, for example, 3-acrylamido-4-nitrobenzeneboronic acid.

A second substrate (304) is adjacent to the volume-responsive hydrogel. The second substrate is deformable in response to the volume change of the hydrogel. The second substrate can deform by deflection towards or away from the third substrate. The deflection can range from about 10 to about 500 µm. The second substrate should be biocompatible and/or pharmaceutically acceptable. The second substrate can be any reversibly deformable elastomer. For example, the second substrate can be a low modulus silicone, neoprene, or isoprene rubber. If a low modulus silicone rubber membrane is used, it may be produced by spin-coating silicone rubber on a silicon wafer. The silicon wafer may be removed entirely or in selective regions by deep etching or base (e.g., KOH) etching.

A third substrate (306) is adjacent to the second substrate and includes a member (308). The member is moveable in response to deformation of the second substrate. The member may be formed by selective etching of a silicon or glass wafer by deep etching or base (e.g., KOH) etching or by mechanical drilling of the substrate. For example, see "Design, Fabrication, and Testing of Micromachined Silicone Rubber Membrane Valves", J. MEMS, Vol 8(4):393-402 (December 1999), which describes fabrication and machining techniques for silicon rubber.

Figure 15:
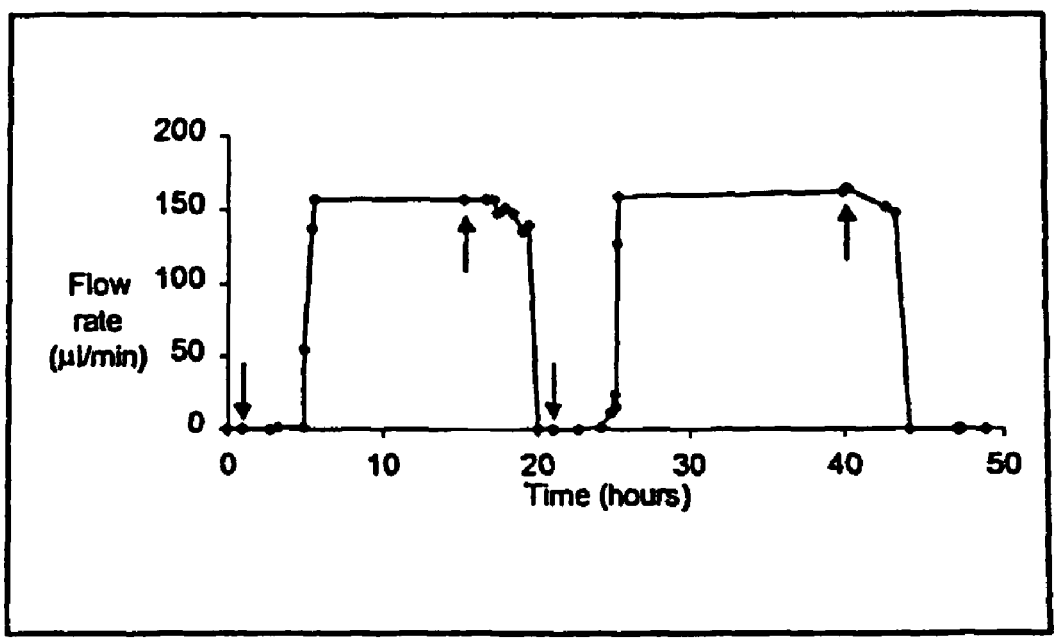
FIG. 15 demonstrates the effect of glucose on fluid flow rate in an embodiment of a hydrogel-actuated microvalve.

A fourth substrate (310) is adjacent to the third substrate and includes an orifice (312) capable of being sealed by the member of the third substrate upon movement of the member. When the orifice is open, fluid can flow through the device. When the hydrogel undergoes a volume increase in response to the predetermined chemical compound, the second substrate deforms by deflection toward the third substrate, resulting in movement of the member of the third substrate. Consequently at least a partial sealing of the orifice in the fourth substrate occurs, affecting fluid flow. Fluid flow may be reduced in the range from about 10% to about 100% upon the deflection of the second substrate and movement of the member of the third substrate. See FIG. 15.

The third and fourth substrate can be manufactured from any material that provides the required structural stability and ability to machine channels and inlet orifices. Preferably, the third and fourth substrate can be manufactured from silicon or glass.

The orifice controls fluid access to a channel (314) disposed between the third and the fourth substrates. The channel may be sized to fix fluid flow when the orifice is open to a predetermined value. For example, the channel may be sized to permit a required dosing regimen in a drug delivery device.

The response time of the microvalve will depend on, without limitation, the thickness and permeability of the first permeable substrate, the exposure of the hydrogel, the hydrogel composition, the thickness of the hydrogel, the deformability of the second substrate, and the gap between the third substrate and the fluid entry orifice in the fourth substrate. The response time can range from about 10 sec. to about 1 hour. The response time will preferably range from about 10 sec. to about 10 mins.

The substrates can be manufactured separately and then assembled. The overall assembly of the microvalve can be performed using various adhesives, including UV-curable adhesives. The assembly can be performed under a light microscope.

Figure 12:
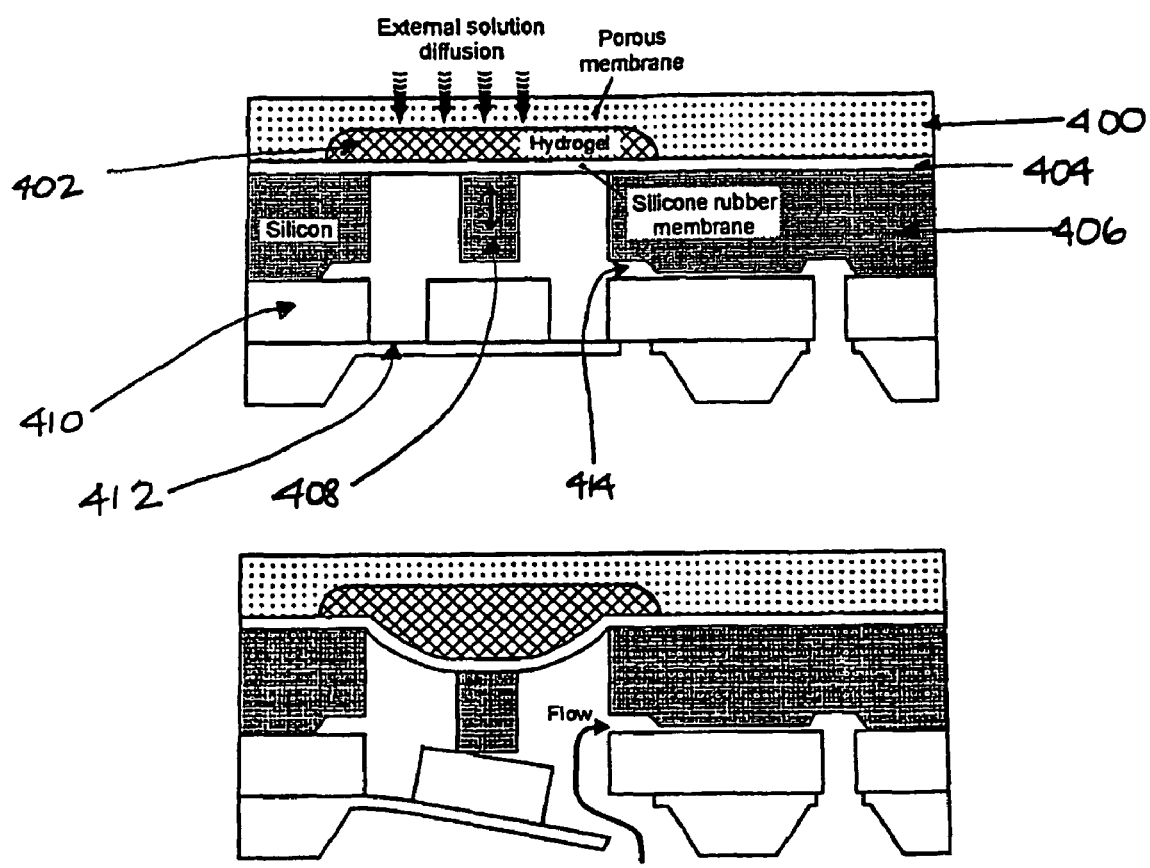
FIG. 12 shows an embodiment of a hydrogel-actuated microvalve where a member is used to move a flexible body to control fluid access to a channel.

Another embodiment of a hydrogel-actuated microvalve is represented in FIG. 12. A first substrate (400) is provided. The first substrate is permeable to a predetermined chemical compound, e.g., glucose. The first substrate can include a porous plate diffusion barrier. Vycor® glass (Corning 7930), Anapore® aluminum oxide, or any other material that can provide homogenous pores in the range from about 10 nm to about 50 μm can be used. The pores should allow the passage of small molecules such as water and buffer components and also the predetermined chemical compound. The first substrate can have a thickness of, for example, from about 50-1000 μm. The first substrate should be resistant to deformation. While not bound by any theory, the first substrate should not relieve the pressure that results from the swelling of the hydrogel; the pressure should instead be transferred to the second substrate to result in deformation of the second substrate. The first permeable substrate provides mechanical support for the hydrogel and prevents its escape from the device, while allowing adequate surface exposure of the hydrogel to the medium.

Adjacent to the first permeable substrate is a volume-responsive hydrogel (402). The volume responsive hydrogel may be trapped in a cavity drilled mechanically (e.g., ultrasonic milling) or etched chemically (e.g., HF 10%) in the first substrate. Alternatively, the hydrogel may be formed in a cavity of an optional support substrate (403) (e.g., silicon or glass) positioned between the first permeable substrate and the second deformable substrate.

The volume-responsive hydrogel is capable of undergoing a volume change in response to the predetermined chemical compound to which the first substrate is permeable. The volume responsive hydrogel can include any of the hydrogel compositions described previously, provided that it demonstrates a volume change (either volume increase or volume decrease) upon exposure to a predetermined chemical compound. For example, the hydrogel can be a glucose sensitive hydrogel that swells upon exposure to glucose; such a hydrogel may include, for example, 3-methacrylamidophenylboronic acid as a responsive composition. Alternatively, the hydrogel may shrink upon exposure to glucose; such a hydrogel may include, for example, 3-acrylamido-4-nitrobenzeneboronic acid.

A second substrate (404) is adjacent to the volume-responsive hydrogel. The second substrate is deformable in response to the volume change of the hydrogel. The second substrate can deform by deflection towards or away from the third substrate. The deflection can range from about 10 to about 500 μm. The second substrate should be biocompatible and/or pharmaceutically acceptable. The second substrate can be any reversibly deformable elastomer. For example, the second substrate can be a low modulus silicone, neoprene, or isoprene rubber. If a low modulus silicone rubber membrane is used, it may be produced by spin-coating silicone rubber on a silicon wafer. The silicon wafer may be removed entirely or in selective regions by deep etching or base (e.g., KOH) etching.

A third substrate (406) is adjacent to the second substrate and includes a member (408). The member is moveable in response to deformation of the second substrate. The member may be formed by selective etching of a silicon or glass wafer by deep etching or base (e.g., KOH) etching or by mechanical drilling of the substrate. For example, see "Design, Fabrication, and Testing of Micromachined Silicone Rubber Membrane Valves", J. MEMS, Vol 8(4):393-402 (December 1999), which describes fabrication and machining techniques for silicon rubber.

A fourth substrate (410) is adjacent to the third substrate and includes a flexible body (412) to control access, upon movement of the member, to a channel disposed between the third substrate and the fourth substrate. When the flexible body is flexed open by the member, fluid can flow through the device. When the hydrogel undergoes a volume increase in response to the predetermined chemical compound, the second substrate deforms by deflection toward the third substrate, resulting in movement of the member of the third substrate and a flexing of the flexible body. Consequently at least partial access to the channel between the third and the fourth substrate results, affecting fluid flow. Fluid flow may be increased in the range from about 10% to about 100% upon the deflection of the second substrate, movement of the member of the third substrate, and flexing of the flexible body.

The third and fourth substrate can be manufactured from any material that provides the required structural stability and ability to machine channels and inlet orifices. Preferably, the third and fourth substrate can be manufactured from silicon or glass. The flexible body can be manufactured from any material that provides the required ability to flex reversibly upon movement of the member.

The flexible body controls fluid access to a channel (414) disposed between the third and the fourth substrates. The channel may be sized to fix fluid flow when the orifice is open to a predetermined value. For example, the channel may be sized to permit a required dosing regimen in a drug delivery device.

The response time of the valve will depend on, without limitation, the thickness and permeability of the first permeable substrate, the exposure of the hydrogel, the hydrogel composition, the thickness of the hydrogel, the deformability of the second substrate, and the gap between the third substrate and the fluid entry orifice in the fourth substrate. The response time can range from about 10 sec. to about 1 hour. Preferably, the response time ranges from about 10 sec. to about 10 mins.

The substrates may be fabricated separately and then assembled. The overall assembly of the microvalve can be performed using various adhesives, including UV-curable adhesives. The assembly can be performed under a light microscope.

The hydrogel-actuated microvalves so constructed provide a means to achieve chemosensitive flow control and adequate environmental exposure of the hydrogel without compromising device integrity.

Figure 13:
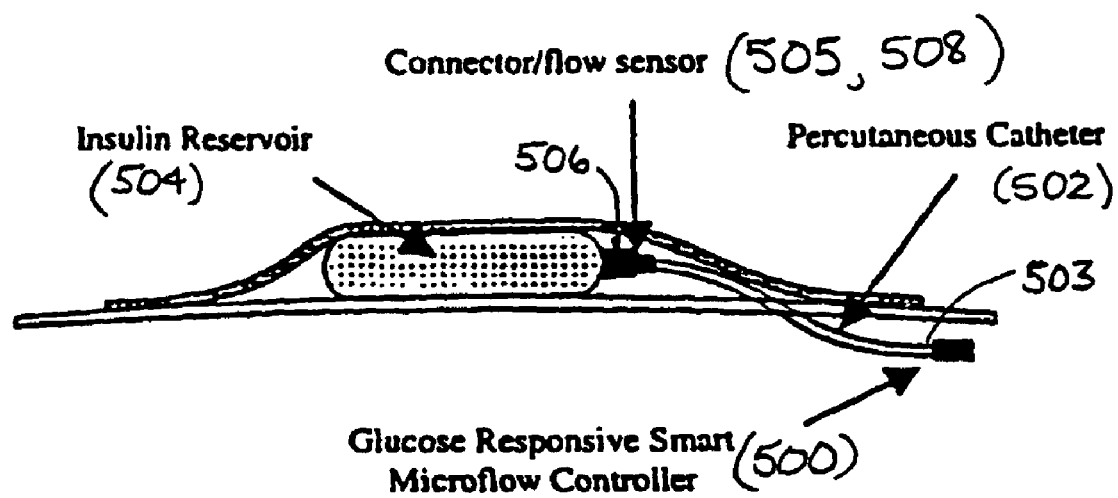
FIG. 13 demonstrates a system for drug delivery according to the present invention.

The invention also provides systems for drug delivery to patients. Referring to FIG. 13, the system includes an implantable, hydrogel-actuated microvalve (500). The hydrogel-actuated microvalve can be any of the microvalves discussed above. A catheter (502) is also provided, with one end of the catheter in communication with the hydrogel-actuated microvalve; the end (503) of the catheter in communication with the microvalve may be positioned intraperitoneally, subcutaneously, or intravascularly in the patient.

A reservoir (504) containing the drug is in communication with the second end (505) of the catheter. The reservoir can be replaced when empty by disconnecting it from the catheter. The reservoir is preferably small enough to be unobtrusive to the patient while providing an appropriate supply of the drug. For example, a 3 mL reservoir is small enough to be unobtrusive while still providing a one week supply of insulin at both basal and bolus rates (~40 units per day).

The drug reservoir may be located outside the body of the patient. Alternatively, the drug reservoir may be positioned subcutaneously on the patient. The variability in positioning allows for flexibility in system design and may promote patient compliance.

The system includes a pump (506) to deliver the drug from the reservoir through the catheter to the hydrogel-actuated microvalve. The pump may be a volatile liquid/bellows pump, an electromechanical pump, or an osmotic pump. Design and construction of the reservoir and pressure generating mechanism (i.e. pump) depend on the hydrogel swelling pressure and thus the particular hydrogel composition used.

The system may further include a flow meter (508) positioned between the reservoir and the microvalve to monitor the flow of the drug. In one embodiment, the system is used to deliver the drug insulin to diabetic patients.

In any of the devices or systems of the present invention, the substrates may be optionally coated with appropriate surfactants or subjected to surface treatment to prevent, for example, denaturation or aggregation of the fluids flowing through the device or system.

Hydrogel-Mediated Pulsatile Hormone Delivery

Controlled drug delivery through the use of implantable microscale medical devices has a number of inherent benefits as compared to traditional methods of administration. In conventional drug administration, drug concentration in the blood increases immediately after the drug is taken, and then decreases with time. The plasma drug concentration achieved with a particular mode of administration implicates both drug toxicity and efficacy, as most drugs have a limited range in which they are both effective and yet nontoxic. Varying drug pharmacokinetic profiles, clearance mechanisms, and in vivo stabilities further limit the therapeutic application of drugs when they are administered in conventional manners, particularly when patient compliance with a particular regimen is a factor.

The controlled release of drugs can be approached in a number of alternative modes. The "gold standard" of controlled release is often considered to be constant delivery of the drug over a set time period (also known as zero-order release), resulting in a constant plasma drug level in the desired therapeutic range. The desirability of this zero-order release mechanism is based on the assumption that there is a direct, time invariant relationship between plasma drug level and effect, and that the therapeutic window is time invariant.

The present invention recognizes, however, that this assumption does not hold in all therapeutic indications, particularly those where a periodic, pulsed delivery of a drug would be preferred. For example, numerous hormones are released endogenously in a periodic, pulsatile manner that is often autonomous from any physiologic parameter. A periodic, pulsed mechanism of delivery would thus mimic closely the in vivo production of many hormones and can better regulate a particular physiologic condition.

Studies have shown that human growth hormone, prolactin, thyroid stimulating hormone, adrenocorticotropic hormone, luteinizing hormone, follicle stimulating hormone, β-endorphin, melatonins, vasopressin, rennin, parathyroid hormone, pancreatic polypeptide, somatostatins, glucagons, estradiol, progesterone, testosterone, aldosterone, and cortisol are all released in pulses at periodic time points throughout the day; such a release profile is termed "ultradian." Studies in cell culture, animal models, and human patients have shown that a hormone's efficacy is related to both the pulse width and interpulse interval of release, and that restoration of an endogenous pattern of hormone secretion is essential for hormone replacement therapy. For example, pulsatile replacement of gonadotropin releasing hormone (GnRH, also known as luteinizing hormone-releasing hormone, LHRH) over extended periods can reverse symptoms of hypogonadotropic hypogonadism (HH), which results in stalled sexual maturation.

Depending on the disease at issue, therefore, the present inventors have recognized that hydrogels can be surprisingly used in two alternative modes of controlled drug delivery: 1) drug delivery directly mediated by hydrogel-response to a pre-determined chemical, physical, or biological parameter; and 2) drug delivery in a pulsed, periodic manner mediated by cycling of a hydrogel-response. Accordingly, the invention takes advantage of the insolubility, open structure, volume-change reversibility, and physical and chemical manipulability of hydrogels in the design of stimulus-responsive and pulsatile drug delivery applications.

Accordingly, in another aspect of the present invention, a hydrogel-mediated device to deliver hormones in a pulsatile manner is provided. The invention imitates the ultradian delivery of hormones in vivo by coupling hormone and glucose diffusional exchange across a pH sensitive hydrogel membrane with rhythmic pH cycling (swelling/deswelling) of the hydrogel. The cycling of pH is achieved with the use of an enzymatic degradation of glucose to gluconate and protons via glucose oxidase. The hydrogel in the swollen state allows diffusional exchange of glucose and hormone, while it prevents diffusional exchange when shrunken. Thus bursts of hormone release are coupled to pH cycling of the hydrogel state.

Figure 16:
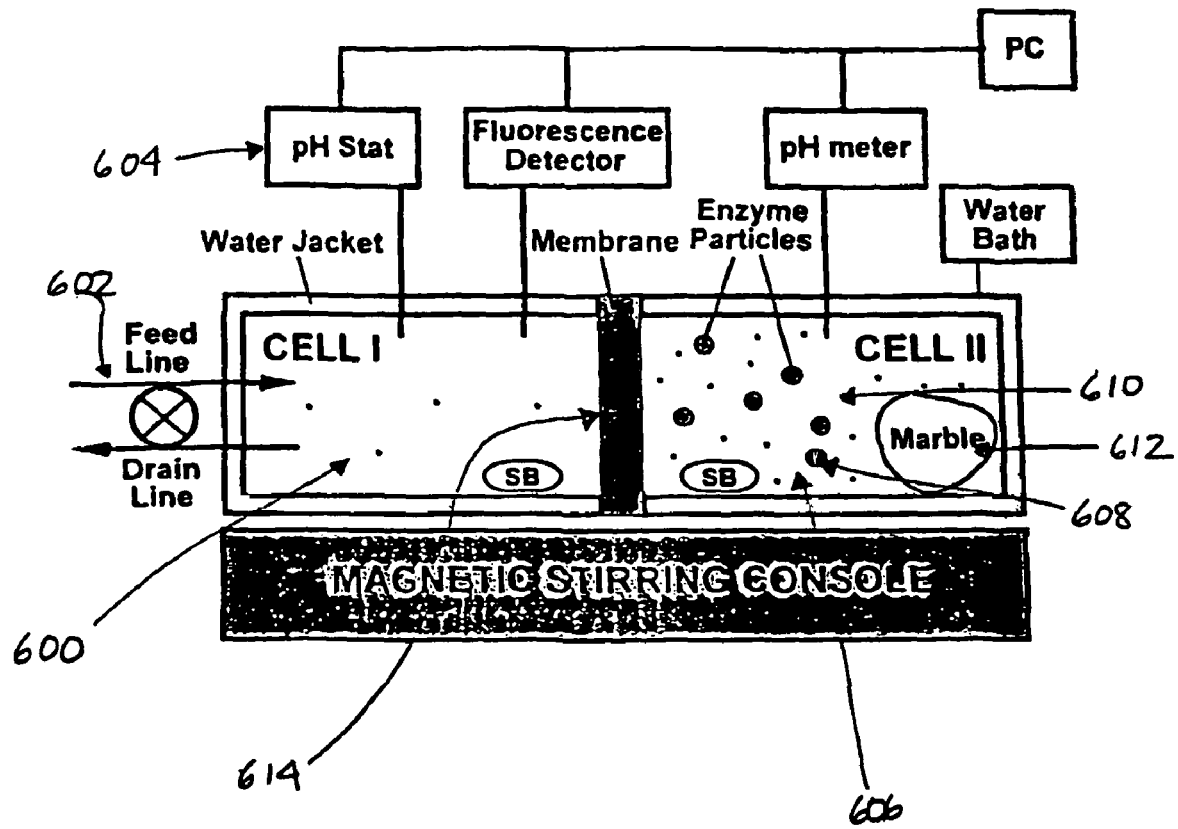
FIG. 16 shows an embodiment of a hydrogel-mediated pulsed hormone delivery device.

Referring to FIG. 16, a first reservoir is provided (600). The first reservoir is connected to a source of glucose (602) and a pH stat (604). The source of glucose provides a glucose solution at a constant concentration. The concentration of glucose can range from about 0.1 mM to about 100 mM. Alternatively, the concentration of glucose can range from about 1 mM to about 50 mM. The pH stat maintains the pH of the first reservoir at a constant pH. The pH stat can maintain the pH of the first reservoir in the range of from about pH 5.5 to about pH 8.0. In another embodiment, the pH stat may maintain the pH of the first reservoir in the range of from about pH 6.5 to pH 7.5. Alternatively, the pH stat maintains the pH of the first reservoir at about pH 7.0.

A second reservoir (606) is also provided. The second reservoir includes a source of glucose oxidase (608), a source of the hormone (610), and a proton sink (612). The source of glucose oxidase may be the enzyme suspended in solution in the reservoir or optionally may be a gel particle comprising glucose oxidase. For example, glucose oxidase can be formulated in acrylamide gel particles by polymerizing acrylamide in the present of glucose oxidase. Catalase and albumin optionally may be included in the gel particles.

The second reservoir also includes a source of a hormone (610). The hormone can be, without limitation, gonadotropin releasing hormone, human growth hormone, prolactin, thyroid stimulating hormone, adrenocorticotropic hormone, luteinizing hormone, follicle stimulating hormone, β-endorphin, melatonin, vasopressin, rennin, parathyroid hormone, pancreatic polypeptide, somatostatin, glucagon, estradiol, progesterone, testosterone, aldosterone, or cortisol. In one embodiment, the hormone is gonadotropin releasing hormone. The hormone may be suspended in solution in the second reservoir, or optionally may be in gel particle form.

The second reservoir also includes a proton sink (612). While not being bound by any theory, it is believed that the presence of the proton sink in the second reservoir facilitates the rhythmic behavior of the hydrogel swelling/deswelling process by accelerating the pH swings in the system and by slowing the approach to a steady state, intermediate permeability hydrogel. The proton sink can include calcium carbonate, magnesium carbonate, potassium carbonate, or sodium carbonate. The proton sink may be in the form of one or more pellets, marbles, particles, etc., or optionally may be dissolved in solution.

A pH-sensitive hydrogel membrane (614) is disposed between the first and second reservoirs. When it is in its swollen state, the pH sensitive hydrogel membrane should permit diffusion of glucose and hormone across itself. When the pH sensitive hydrogel membrane is collapsed or shrunken, it should limit diffusion of both glucose and the hormone across the membrane. One embodiment of a pH-sensitive hydrogel comprises polymerized N-isopropylacrylamide (NIPA), methacrylic acid (MAA), and ethylene glycol dimethyacrylate (EGDMA).

The pH sensitivity of the hydrogel membrane results in a volume-decrease of the hydrogel at a pH range from about pH 7.4 to about pH 3.5. Alternatively, the volume-decrease can occur at a pH range from about pH 5.5 to about pH 3.5.

EXAMPLES

Example 1

Fabrication and Formation of a Hydrogel Microscale Component

Fabrication. A 5 mm wide×5 mm long×500 μm thick Pyrex® glass wafer was used. A first set of four 300 μm deep trenches (120 μm wide, 200 μm apart) were etched with a deep etching technique on one surface of the wafer. On a second surface of the wafer, a second set of four 300 μm deep trenches (120 μm wide, 200 μm apart) were etched with a deep etching technique in an orientation perpendicular to the first set.

Introduction and polymerization of a liquid polymerizable mixture. A pregel solution containing 3-methylacrylamidophenylboronic acid, acrylamide, and N,N' methylenebisacrylamide was loaded into the channels and the wafer was sandwiched between two glass slides. The solution was then polymerized and the glass slides removed. The device was equilibrated in 0.015 M phosphate buffered saline (PBS), pH 7.4. FIG. 5 shows a free-swelling profile of such glucose-sensitive hydrogel in 0.015 M PBS.

Effect of glucose on flow rate. FIG. 6 shows the flow rate of PBS solution through the device in the presence and absence of glucose. PBS (0.015 M) solutions with and without 5 mM glucose were allowed to flow through the device alternatively, and the flow rate was measured. In the absence of glucose, the flow rate was approximately 26 μL/min, suggesting an open gate. In the presence of 5 mM glucose, the flow rate decreased to about 6 μL/min, suggesting a closed gate.

Figure 17:
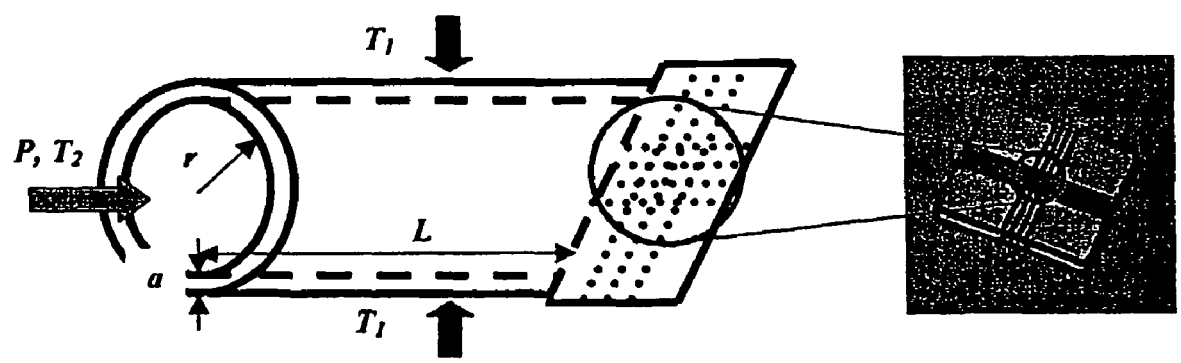
FIG. 17 is a schematic of an oscillatory flow control system with a temperature-sensitive hydrogel microscale component.

Demonstration of Oscillatory Flow Pattern:

A hydrogel microscale component can be employed as part of a device to control fluid flow based on a pre-determined stimulus, e.g., temperature or pH changes. The microscale device can demonstrate an oscillatory pattern of fluid flow in response to the pre-determined stimulus. Generally, as shown in FIG. 17, a stimulus-sensitive hydrogel microscale component can be attached to a tube with an inner radius r and wall thickness a. The tube can transport a desired liquid to the hydrogel microscale component. A segment of the tube and the microscale component can be maintained at a desired temperature $T_1$, e.g., immersed in a liquid of temperature $T_1$, e.g., immersed in a water bath. A liquid of interest for delivery with a temperature of $T_2$ can then be fed through the tube to the temperature sensitive hydrogel microscale component. The liquid may be delivered at varying hydraulic pressures, e.g, at an hydraulic pressure of 2 kPa.

Figure 18:
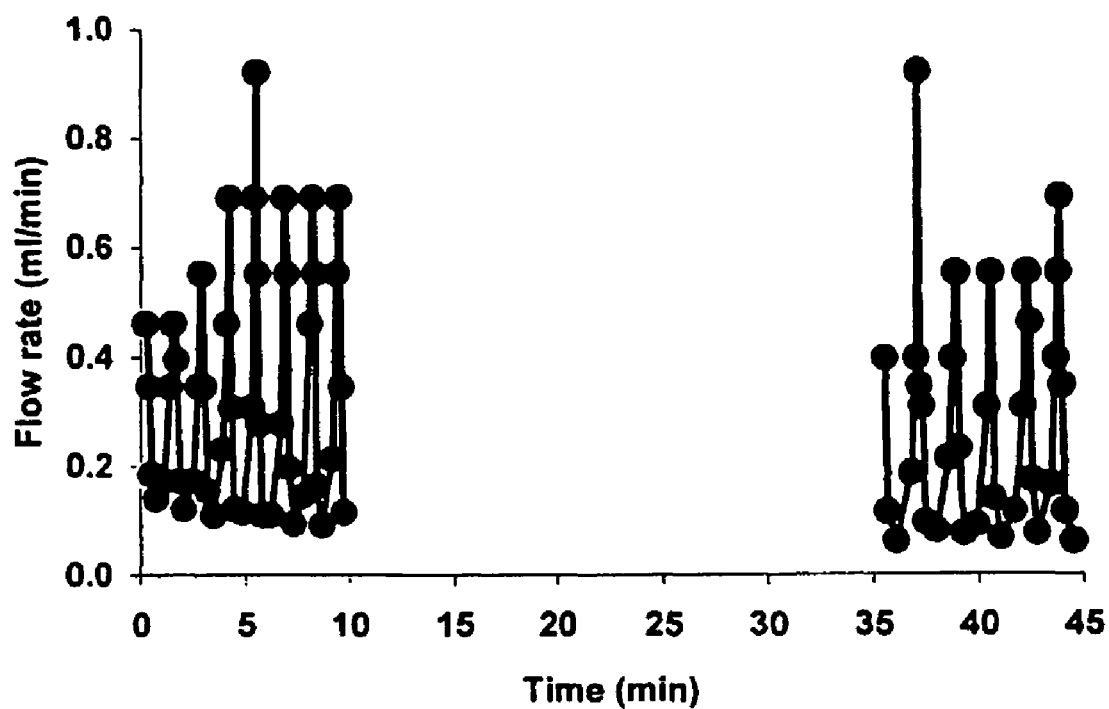
FIG. 18 demonstrates the oscillatory flow control achieved by maintaining a temperature gradient between the liquid supplied to the microscale component and the temperature at which the microscale component is maintained.

As can be seen from FIG. 18, a regular oscillatory flow pattern can be achieved with such a microscale component. In this embodiment, a silicone tube is used, and a poly(N-isopropylacrylamide) hydrogel (100 mg isopropylacrylamide (NIPA), 1 mg N,N'-methylenebisacrylamide (Bis), 5 μl N,N,N',N'-tetramethylethylenediamine (TEMED), and 1 mg ammonium persulfate (APS) dissolved in 1 mL deionized water) with a volume phase transition temperature at 32-34° C. is loaded into the hydrogel microscale component. The microscale component has channels 120 μm wide and 180 μm apart. The working area (inside the circle shown in FIG. 17) is 1 mm×1 mm. Water is fed through the tube at a hydraulic pressure of 2 kPa. The relevant parameters are: a=0.75 mm; r=1 mm; L=2.3 cm; $T_1$=35.1° C.; $T_2$=6° C. and P=2 kPa.

The oscillatory flow pattern can be explained as follows. A NIPA hydrogel undergoes a volume collapse when the temperature exceeds 34° C., and reswells when the temperature drops below that point. When cold water is introduced through the tube, it causes the hydrogel to swell and cut off fluid flow. A period in which the intraluminal water is heated by passive conduction from the surrounding water bath then follows, until the intraluminal water temperature exceeds 34° C. At this point, the hydrogel collapses, again allowing fluid flow through the device. Warm water is replaced by cold water, which reswells the hydrogel and stops flow, thus reinitiating the cycle.

Example 2

Fabrication and Formation of a Hydrogel Microscale Component

Fabrication. A 2 μm Low Pressure Chemical Vapor Deposition (LPCVD) low stress nitride deposition on standard <100> silicon wafers was performed. The backside nitride was patterned and the silicon etched in KOH until 100 μm thick silicon membranes were obtained. Next, the front side nitride was patterned with the features shown in FIGS. 3 and 4, and the silicon so etched in a deep trench etcher. During this step the central circle in the pattern defines a substrate member (e.g., post) whereas the four radial projections define thin silicon walls; the open areas are structured orifices. Subsequently, a short KOH-etch undercut the thin walls into triangular shape tethers. Finally, a second deep trench etch opened the orifices to the other side of the membrane and defined a second set of tethers. Loading of the hydrogel was achieved by immersing the microscale component in a small amount of pre-gel solution and waiting until it polymerized. The excess hydrogel was easily peeled off from both sides of the membrane.

Hydrogels: The following hydrogels were used:

Temperature-sensitive: 100 mg isopropylacrylamide (NIPA), 1 mg N,N'-methylenebisacrylamide (Bis), 5 µl N,N,N',N'-tetramethylethylenediamine (TEMED), and 1 mg ammonium persulfate (APS) dissolved in 1 mL deionized water.

Glucose-sensitive: 80 mg acrylamide (AAm), 52 mg 3-methylacrylamidophenylboronic acid (MPBA), 0.5 mg Bis, 5 µl TEMED, and 0.5 mg APS dissolved in 0.7 mL deionized water.

Figure 19A:
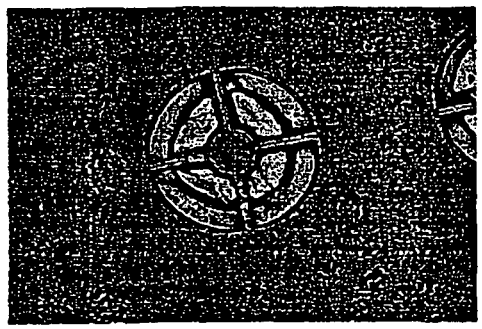
FIG. 19 shows micrographs of a microscale component loaded with a temperature-sensitive hydrogel at a) 50° C. (hydrogel shrunken); and b) 25° C. (hydrogel swollen).
Figure 19B:
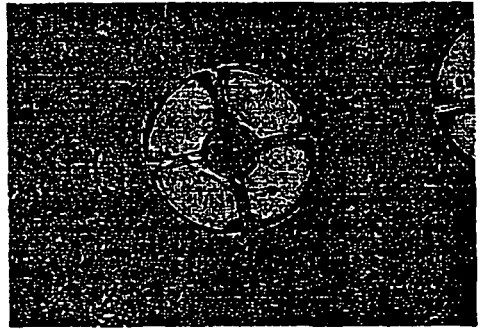

Effect of temperature and glucose on flow rate—FIG. 19 demonstrates a micrograph of the microscale component loaded with a temperature-sensitive hydrogel (NIPA, phase transition 34° C.) and immersed in water at a) 50° C. (hydrogel shrunken), and b) 25° C. (hydrogel swollen). In the shrunken state (high temperature), the hydrogel is opaque and can be seen around the central substrate member inside the orifices. In the swollen state (low temperature), the hydrogel is transparent and cannot be seen.

Figure 20:
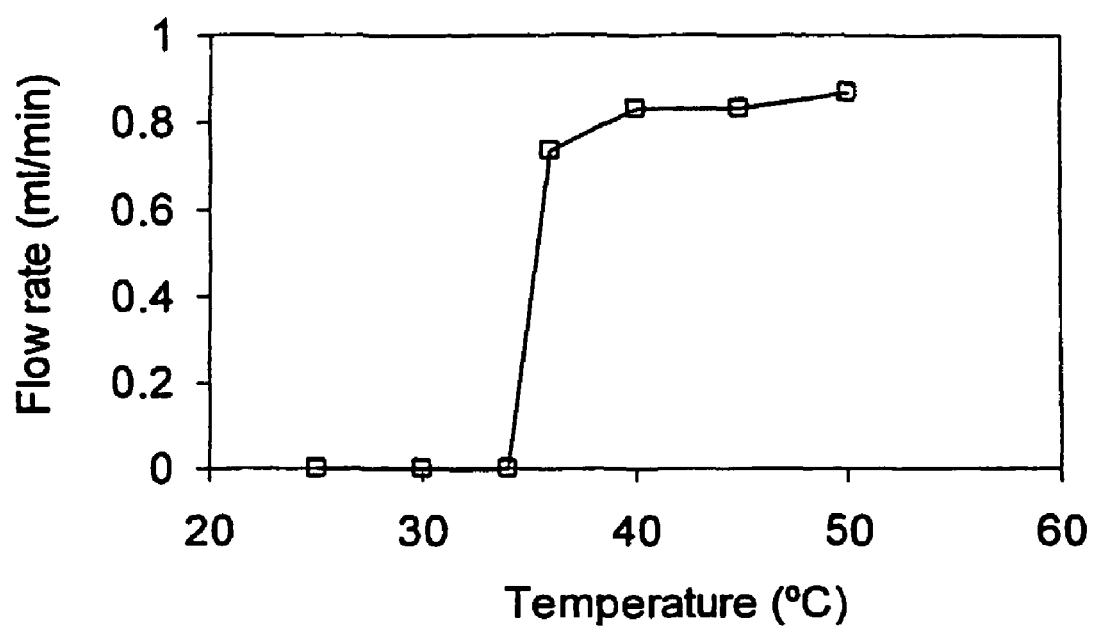
FIG. 20 demonstrates the flow rate vs. temperature curve of the microscale component of FIG. 19.
Figure 21:
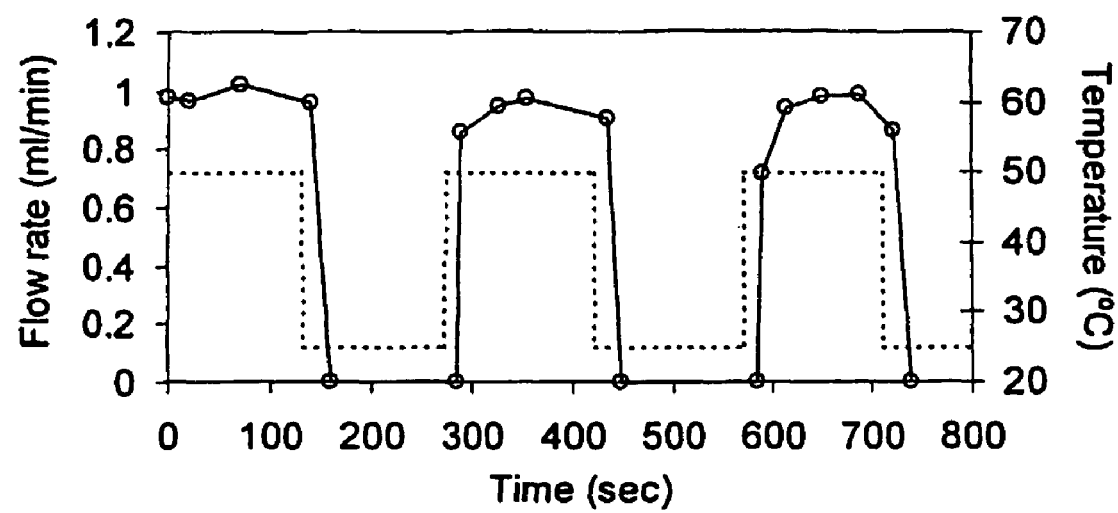
FIG. 21 demonstrates the flow rate vs. time of the microscale component of FIG. 19 as the temperature is alternated between 25° C. and 50° C.
Figure 22:
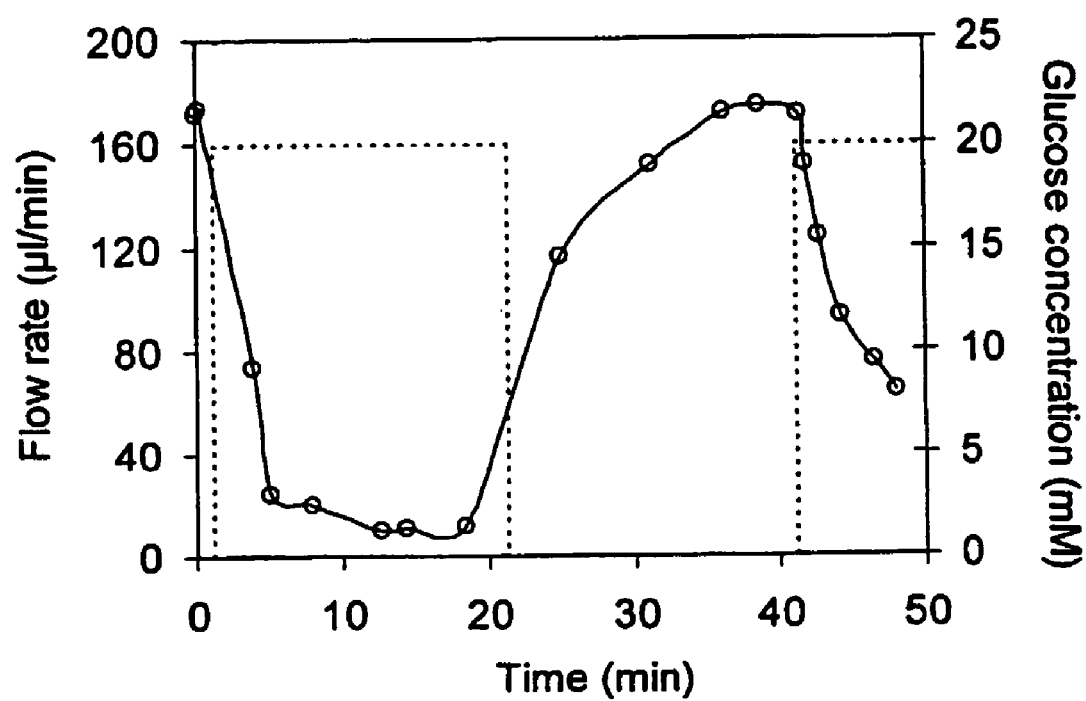
FIG. 22 demonstrates the flow rate vs. time of the microscale component of FIG. 19, loaded with a glucose-sensitive hydrogel, as the glucose concentration is alternated between 0 mM and 20 mM.

FIGS. 20 and 21 show the response of the microscale component loaded with the temperature-sensitive hydrogel described above. The phase transition of this hydrogel occurs at 34° C., which corresponds very well with the sharp flow change of the microvalve at this temperature. The response time is about 10 seconds for opening and 20 seconds for closing. FIG. 22 shows the response of the microscale component loaded with the glucose-sensitive hydrogel described above. Note that the response times are longer due to the need for glucose to diffuse into the hydrogel.

Example 3

Fabrication and Testing of a Hydrogel-Actuated Microvalve

Preparation. Vycor® 7930 glass was used as the first porous substrate. The deformable second substrate was formed by spinning and curing a silicone rubber layer on top of a silicon wafer and combining KOH etch and deep RIE to remove the silicon under the membrane. A third substrate silicon member (embossment) was left at the center. A V-shaped microchannel was created during the KOH etch to fix the flow (or dosing) rate in the open state to a predetermined value. The hydrogel cavity was formed by mechanically drilling (ultrasonic milling) or by etching chemically (HF 10%) the Vycor plate. The hydrogel was a glucose-sensitive hydrogel containing 3-methylacrylamidophenylboronic acid as the responsive composition. The hydrogel was thermally cured inside a mold with suitable dimensions and placed on top of the deformable second substrate silicone membrane prior to mounting of the Vycor® plate. The fourth substrate (Pyrex® glass) had drilled inlet and outlet orifices and was fabricated separately. The overall assembly of substrates was performed using various adhesives under a light microscope.

Figure 14:
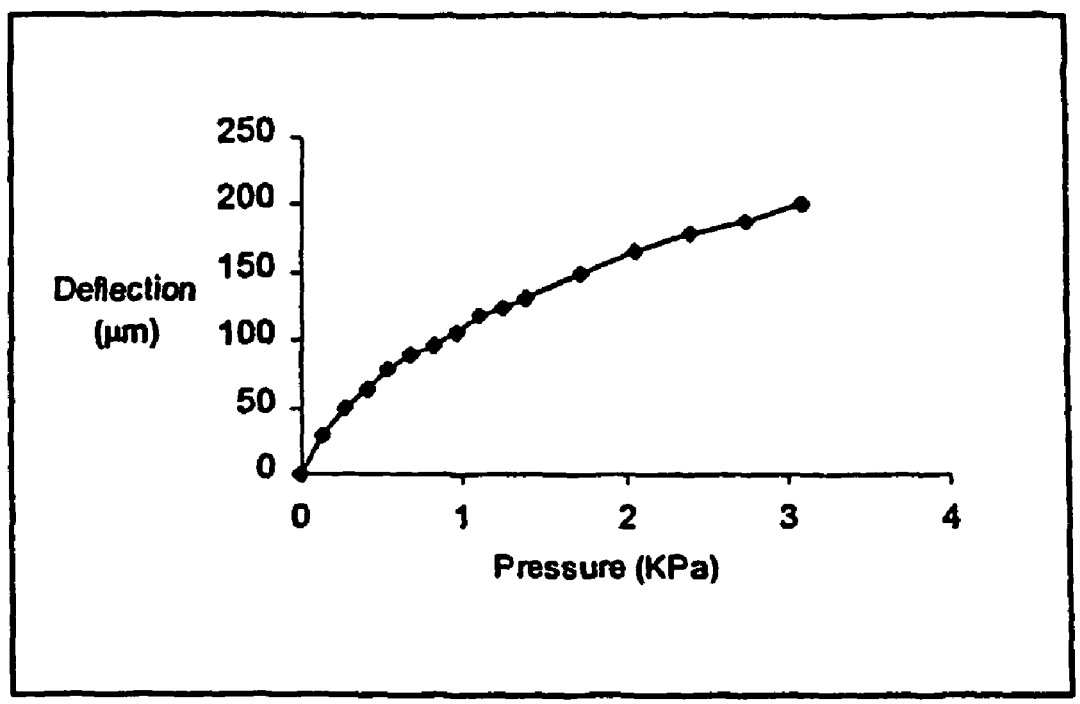
FIG. 14 demonstrates the deflection with pressure of a low modulus silicone rubber membrane substrate of one embodiment of the present invention.

Deflection of the deformable membrane with pressure. FIG. 14 demonstrates the deflection of the silicone membrane (up to 200 µm) measured by applying pressure to the external side and measuring the displacement of the silicon member.

Response of the hydrogel-actuated microvalve to glucose. A 500 µm thick glucose-responsive (containing 3-methylacrylamidophenylboronic acid) hydrogel was used in the above microvalve device. The microvalve was immersed alternately in phosphate buffered saline (PBS) solutions containing 0 or 20 mM glucose. The response time of the valve was about 4 hours. See FIG. 15 (note that downward arrows mark the change from 20 mM to 0 mM glucose, while upward arrows mark the change from 0 mM to 20 mM glucose).

In similar experiments with a 200 µm thick hydrogel, the response time was about 45 mins.

Example 4

Fabrication and Testing of a Hydrogel-Mediated Pulsatile Delivery Device

Preparation. Hydrogel membranes were formed by polymerizing N-isopropylacrylamide (NIPA, Kodak), methacrylic acid (MAA, Polysciences), and ethylene glycol dimethyacrylate (EGDMA, Polysciences) with molar composition 90/10/0.7 respectively in 1 mL 50/50 w/w water/methanol, with cosolvent mass twice that of comonomer mixture. Polymerization was initiated with 5 mg ammonium persulfate (APS, Polysciences) and 20 µL tetraethylmethylenediamine (TEMED, Aldrich) and was performed at 10° C. between glass plates separated by a 250 µm spacers. Membranes were extensively washed and conditioned in saline.

Small polyacrylamide gel particles containing glucose oxidase (GluOx, Sigma, 234 IU/mg) and catalase (Cat, Sigma, 10,700 IU/mg) were polymerized at 4° C. with 1 mL water, 0.2 gm acrylamide (Sigma), 5 µL EGDMA, 4 mg APS, 10 µL TEMED, 10 mg Albumin (Sigma), 20 mg GluOx and 2 mg Cat.

Pulsatile delivery of ƒ-GnRH Membranes were mounted in a water-jacketed, side-by-side diffusion cell with transport aperture radius of 1 cm, as shown in FIG. 16. Before an experimental run, both Reservoir I and Reservoir II were filled to 80 mL with 50 mL NaCl solution containing 0.01 w % 2-bromo-2-nitro-1,3-propanediol (bronopol, antibacterial, Aldrich) and a steady pH gradient was established across the membrane by pH stat-ing Reservoir I and Reservoir II at pH 7.0 and 4.5, respectively.

At the start of the run, the pH stat was disconnected from Reservoir II. Gel/enzyme particles and a 12.5 gm piece of marble ($CaCO_3$) were placed in Reservoir II, and tetramethylrhodamine-labeled gonadotropin releasing hormone (f-GnRH, MW-1614, Genemed Sciences, Inc.) was spiked into Reservoir II to concentration of 1 µM. Glucose was spiked into Reservoir I to concentration of 50 mM. A solution containing 50 mM glucose, 50 mM NaCl, and 0.01 w % bronopol was then circulated through Reservoir I using a peristaltic pump (SciLog) with flow rate 1.36-1.38 mL/min.

During a run, pH in Reservoir II was followed with a pH electrode, and the appearance of f-GnRH in Reservoir I was monitored spectrofluorimetrically ($\lambda_{ex}$=520 nm, $\lambda_{em}$=572 nm). Vigorous stirring was provided, and temperature was maintained at 37° C.

Figures 23A, 23B:
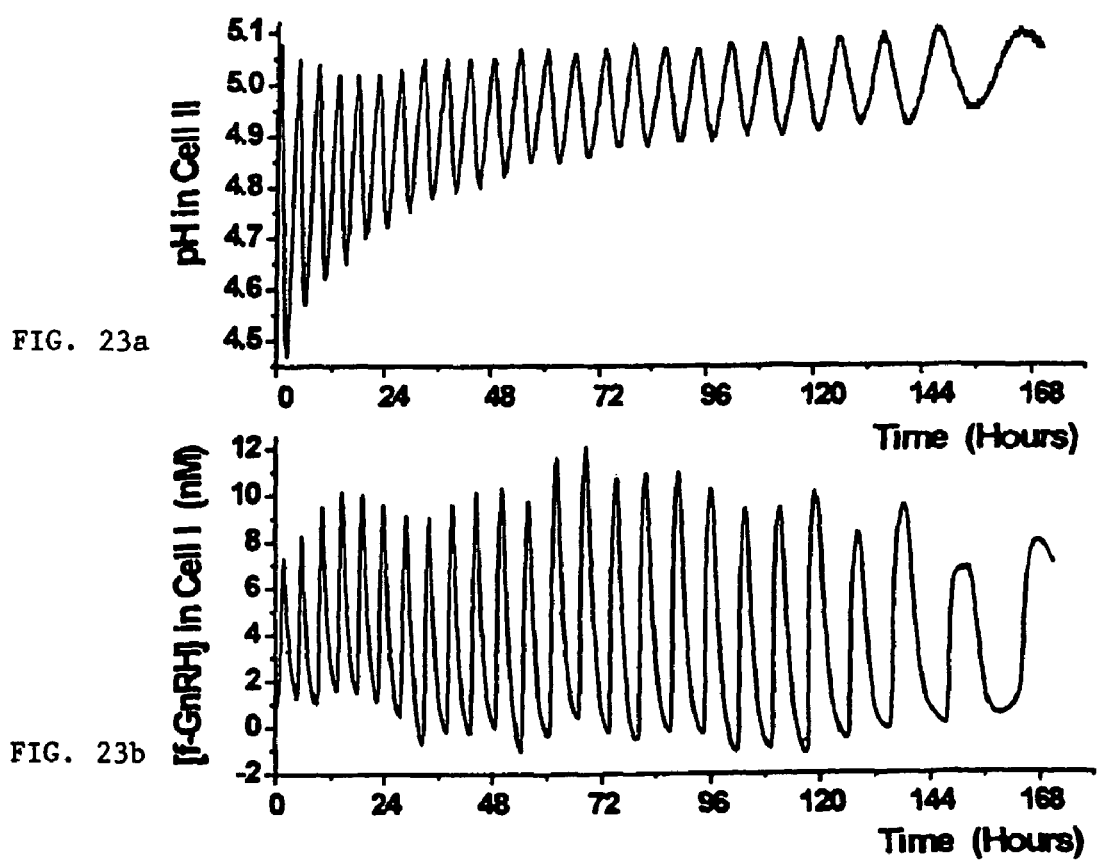
FIG. 23 demonstrates the time course of pH fluctuation (FIG. 23a) and the time course of release of gonadotropin releasing hormone (GnRH) (FIG. 23b) in an embodiment of a hydrogel-mediated pulsed hormone delivery device.

FIG. 23 shows the results of a typical run. The pH record in Reservoir II (FIG. 23a) is characterized by troughs that become progressively shallower but convergent, and peaks that converge rapidly to a near-constant value. The period between pH peaks steadily increases from approximately 4 hours initially to 8-12 hours at about one week, after which pH oscillations cease. FIG. 23b shows a series of pulses of f-GnRH concentration in Reservoir I that correlate with pH drops in Reservoir II. When pH increases in Reservoir II, f-GnRH transport ceases, and the decay in f-GnRH concentration in Reservoir I reflects washout through the circulation drain line.

Figure 24:
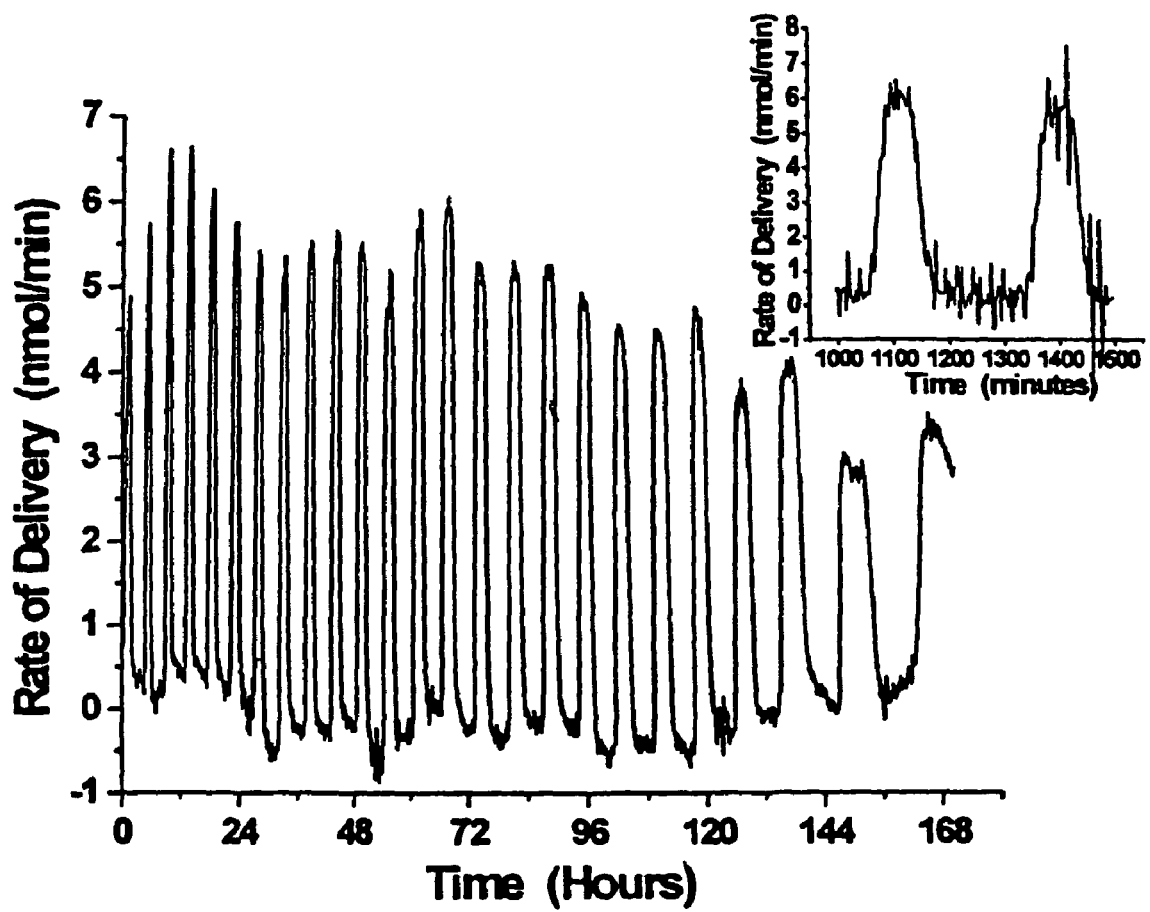
FIG. 24 demonstrates the rate of delivery of GnRH through an embodiment of a hydrogel-mediated pulsed hormone delivery device.

The rate of release of f-GnRH across the membrane was estimated from the record in FIG. 13b by deconvoluting the residence time distribution (rtd) of hormone in Reservoir I. Since Reservoir I was well-stirred with constant volume (80 mL) and constant outflow rate (F=1.37 mL/min), the rtd is given by (F/V)exp(−Ft/V). Results, shown in FIG. 24, feature bursts of f-GnRH release separated by quiescent interpulse intervals. Peak width and interpeak interval increase with time.

It is noteworthy that this system behaves rhythmically even though no rhythmic stimulus is applied. In particular, glucose is fed at a constant concentration. The system therefore differs from systems which respond to changes in glucose concentration.

Rhythmic behavior is attributed to nonlinear negative feedback between membrane and enzyme. When pH in Reservoir II is sufficiently high, the NIPA/MAA membrane is charged and swollen, and permeable to glucose, which enters Reservoir II and is enzymatically converted to gluconate and protons, resulting in a pH drop in Reservoir II. Protons bind to and neutralize MAA groups on the membrane, which then deswells under the influence of the hydrophobic NIPA component. The membrane is now impermeable to glucose, and production of protons is attenuated, as signaled by increasing pH in Reservoir II. Eventually protons bound to the membrane diffuse into Reservoir I, the membrane's charge and permeability are restored, and the cycle is poised to repeat. Cycles of swelling and deswelling correspond respectively to permeation and blockage of f-GnRH into Reservoir I.

The pH oscillations in Reservoir II are accompanied by coherent alterations in the membrane's stiffness, which can be observed since the membrane exhibits small vibrations in response to the hydrodynamic agitation derived from stirring.

Figure 25:
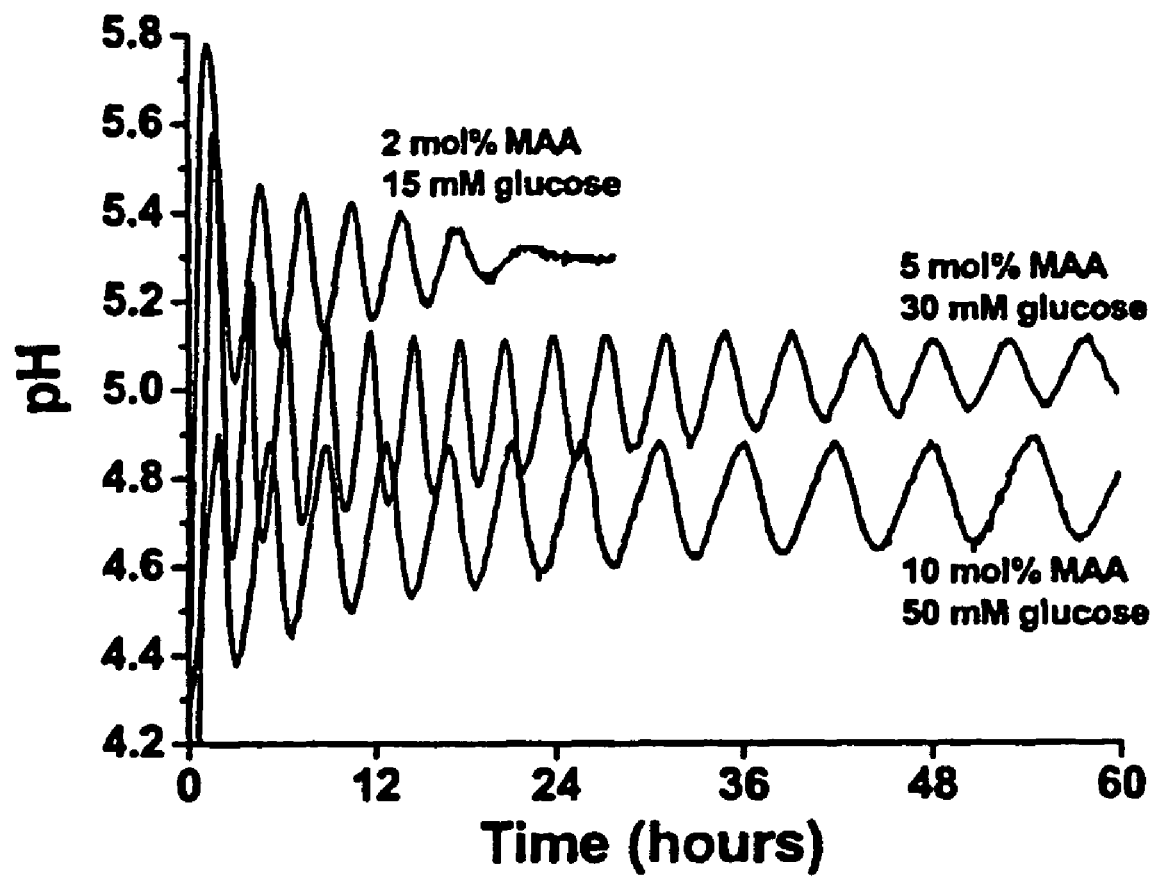
FIG. 25 demonstrates the effect of MAA and glucose concentration on pH oscillations in an embodiment of a hydrogel-mediated pulsed hormone delivery device.

The pH range over which oscillations occur may be shifted in the alkaline direction by reducing MAA content in the membrane. Similarly, glucose feed concentrations necessary to elicit oscillations are reduced with decreasing MAA content. See FIG. 25. The alkaline shift in pH-oscillations and the lower glucose concentrations in Reservoir I necessary to elicit oscillations with decreasing MAA content in the membrane may be explained in terms of the competition between hydrophobic and electrostatic/osmotic forces governing swelling and collapse. At constant ionic strength and temperature, the relative strengths of these forces in a hydrogel are determined primarily by the fixed charge density of the hydrogel membrane, which is the product of the mole fraction of MAA in the polymer and the fraction of MAA groups that are ionized, the latter increasing with pH. It follows that reducing MAA content in the membrane will result in an alkaline shift in the hysteresis band, and hence the range of pH oscillations. To target pH in Reservoir II into an increasingly alkaline range, the concentration of glucose in Reservoir I must be reduced, as this leads to decreased flux of glucose into Reservoir II and reduced enzymatic production of protons.

A number of embodiments of the invention have been described. Nevertheless, it will be understood that various modifications may be made without departing from the spirit and scope of the invention. Accordingly, other embodiments are within the scope of the following claims.

What is claimed is:

1. An implantable, hydrogel-actuated microvalve comprising:
   (a) a first substrate permeable to a predetermined chemical compound;
   (b) a volume-responsive hydrogel adjacent to the first substrate permeable to the predetermined chemical compound, the volume-responsive hydrogel undergoing a volume change in response to the predetermined chemical compound;
   (c) a second substrate adjacent to the volume-responsive hydrogel, the second substrate deformable in response to the volume-responsive hydrogel; and
   (d) a third substrate adjacent to the second substrate, the third substrate comprising an orifice capable of being sealed by the second substrate upon the deformation of the second substrate in response to a change in volume of the hydrogel.

2. An implantable, hydrogel-actuated microvalve comprising:
   (a) a first substrate permeable to a predetermined chemical compound;
   (b) a volume-responsive hydrogel adjacent to the first substrate permeable to the predetermined chemical compound, the volume-responsive hydrogel undergoing a volume change in response to the predetermined chemical compound;
   (c) a second substrate adjacent to the volume-responsive hydrogel, the second substrate deformable in response to the volume-responsive hydrogel;
   (d) a third substrate adjacent to the second substrate, the third substrate comprising a member, the member moveable in response to deformation of the second substrate in response to a change in volume of the hydrogel;
   (e) a fourth substrate adjacent to the third substrate, the fourth substrate comprising an orifice capable of being sealed by the member of the third substrate upon movement of the member.

3. An implantable, hydrogel-actuated microvalve comprising:
   (a) a first substrate permeable to a predetermined chemical compound;
   (b) a volume-responsive hydrogel adjacent to the first substrate permeable to the predetermined chemical compound, the volume-responsive hydrogel capable of undergoing a volume change in response to the predetermined chemical compound;
   (c) a second substrate adjacent to the volume-responsive hydrogel, the second substrate deformable in response to the volume-responsive hydrogel;
   (d) a third substrate adjacent to the second substrate, the third substrate comprising a member, the member moveable in response to deformation of the second substrate; and
   (e) a fourth substrate adjacent to the third substrate, the fourth substrate comprising a flexible body, the flexible body controlling access, upon cooperative movement of the member with the volume-responsive hydrogel, to a channel disposed between the third substrate and the fourth substrate.

4. The hydrogel-actuated microvalve of any one of claims 1-3, wherein the first substrate is resistant to deformation.

5. The hydrogel-actuated microvalve of any one of claims 1-3, wherein the first substrate comprises a porous glass plate.

6. The hydrogel-actuated microvalve of any one of claims 1-3, wherein the first substrate comprises a porous aluminum oxide plate.

7. The hydrogel-actuated microvalve of any one of claims 1-3, wherein the first substrate comprises a porous plate having homogenous pores in the range of about 10 nm to about 50 µm.

8. The hydrogel-actuated microvalve of any one of claims 1-3, wherein the first substrate comprises a porous plate having a thickness of about 50 to about 1000 µm.

9. The hydrogel-actuated microvalve of any one of claims 1-3, wherein the volume-responsive hydrogel undergoes a volume increase or a volume decrease in response to the predetermined chemical compound glucose.

10. The hydrogel-actuated microvalve of claim 9, wherein the hydrogel comprises 3-methacrylamidophenylboronic acid and wherein the hydrogel undergoes a volume increase in response to glucose.

11. The hydrogel-actuated microvalve of claim 9, wherein the hydrogel comprises 3-acrylamido-4-nitrobenzeneboronic acid and wherein the hydrogel undergoes a volume decrease in response to glucose.

12. The hydrogel-actuated microvalve of any one of claims 1-3, wherein the second substrate is selected from the group consisting of a low modulus silicone, neoprene, and isoprene rubber.

13. A catheter comprising the hydrogel-actuated microvalve of any one of claims 1-3.

* * * * *

UNITED STATES PATENT AND TRADEMARK OFFICE
CERTIFICATE OF CORRECTION

PATENT NO. : 7,988,685 B2
APPLICATION NO. : 10/494119
DATED : August 2, 2011
INVENTOR(S) : Babak Ziaie Page 1 of 1

It is certified that error appears in the above-identified patent and that said Letters Patent is hereby corrected as shown below:

Column 1, Line 9, please delete "PCT/US02/35169" and insert -- PCT/US02/35159 --, therefor.

Signed and Sealed this
Fourteenth Day of February, 2012

David J. Kappos
*Director of the United States Patent and Trademark Office*